(12) United States Patent
Parang et al.

(10) Patent No.: US 7,351,731 B2
(45) Date of Patent: Apr. 1, 2008

(54) AZOLE DERIVATIVES AND METHODS FOR MAKING THE SAME

(75) Inventors: Keykavous Parang, Wakefield, RI (US); Soroush Sardari, Tarbes (FR); Nguyen Hai Nam, Hanoi (VN)

(73) Assignee: Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 239 days.

(21) Appl. No.: 11/289,348

(22) Filed: Nov. 29, 2005

(65) Prior Publication Data

US 2006/0142361 A1  Jun. 29, 2006

(51) Int. Cl.
*A61K 31/4196* (2006.01)
*C07D 249/08* (2006.01)

(52) U.S. Cl. ............... 514/383; 548/262.2; 548/267.8; 548/268.6

(58) Field of Classification Search ............ 548/262.2, 548/267.8, 268.6; 514/383
See application file for complete search history.

(56) References Cited

U.S. PATENT DOCUMENTS

| 4,992,454 A | 2/1991 | Richardson et al. |
| 6,063,933 A | 5/2000 | Karimian et al. |

*Primary Examiner*—Golam M. M. Shameem
(74) *Attorney, Agent, or Firm*—Gauthier & Connors, LLP

(57) ABSTRACT

The present invention is broadly directed to azole derivatives that exhibit antifungal activity and methods for making the same. In one aspect, the invention includes carboxylic acid and phosphate ester derivatives of fluconazole that exhibit antifungal activity. In addition, the invention comprises methods for synthesizing the derivatives and pharmaceutical compositions containing the derivatives.

2 Claims, 4 Drawing Sheets

AZOLE DERIVATIVES AND METHODS FOR MAKING THE SAME

PRIORITY DATA

This application claims the benefit of International Patent Application Serial No. PCT/US2004/23316 filed on Jul. 19, 2004, U.S. Provisional Patent Application Ser. No. 60/543,972 filed on Dec. 2, 2004 and U.S. Provisional Patent Application Ser. No. 60/488,319 filed on Jul. 18, 2003.

BACKGROUND OF THE INVENTION

The invention relates to azole derivatives and methods for making the same and more specifically to carboxylic acid and phosphate ester derivatives of fluconzaole and voriconazole and methods for making the same. This invention further relates to use of the voriconazole and fluconazole derivatives as anti-fungal agents.

In recent years fungal infections have emerged as a major cause of disease and mortality, in part as a consequence of the increase in acquired immunodeficiency syndrome (AIDS), the greater use of immunosuppressive drugs, the long term use of corticosteroids, and even the indiscriminate use of antibiotics. Fridkin et al., *Clin. Microbiol Rev.* 1996, 9, 499; Larocco, M. T. et al., *Clin. Microbiol. Rev.* 1997, 10, 277; Patel et al., C. V. *Clin. Microbiol. Rev.* 1997, 10, 86. There are effective antifungal agents in the market, but each drug carries several drawbacks. The presently marketed antifungal drugs are either highly toxic (e.g., amphotericin B, A MB) or are becoming ineffective due to appearance of resistant strains (e.g. flucytosine and azoles). AMB remains the "gold standard" drug for life-threatening fungal infections, but its use is limited due to its severe toxicity and the inconvenience of intravenous dosing. Perfect, J. R. et al, *Drug Safety* 1992, 7, 323; Sabra, R. et al., *Drug Safety* 1990, 5, 94. Fluconazole (FLC) is an orally effective azole-based antifungal drug with low toxicity, (Kauffman, C. A. et al., *Drugs* 1997, 53, 539) but it has a limited antifungal spectrum and is not fungicidal. Although FLC shows efficacy against *Candida albicans* and *C. neoformans*, it is not very effective against *Aspergillus niger* (Schmitt, H. J. et al, *Chemotherapy* 1992, 38, 118; Zakula, D.; Capobianco, J. O. et al., *Antimicrobial Chemotherapy* 1997, 39, 261) and *Aspergillus fumigatus*. Tsukuda, T. et al., *Bioorg Med. Chem. Lett.* 1998, 8, 1819. In addition, extensive use of FLC has increased the number of F LC-resistant *C. albicans* isolates. Rex, J. H. et al., *Antimicrob. Agents Chemother.* 1995, 39, 1.

Therefore, toxicity concerns, limited spectrum, and the emergence of fungi resistant to currently available agents have created a need for antifungal agents and in particular antifungal agents effective against life-threatening systemic mycoses caused by *C. neoformans, Aspergillus* species, and *Candida* species.

SUMMARY OF THE INVENTION

Broadly, the invention comprises derivatives of fluconazole that exhibit antifungal activity.

In one aspect, the invention comprises carboxylic acid and phosphate ester derivatives of fluconazole that exhibit antifungal activity.

In another aspect, the invention comprises a compound of the following structure:

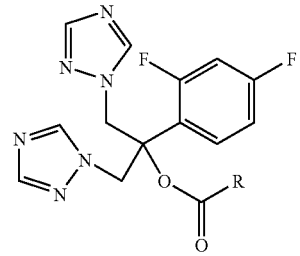

(1)

wherein R i s an alkyl, aryl, alkene, alkyne, a substituted alkene, a substituted alkyl, a substituted aryl, a substituted alkyne, an alkyl halide, alkoxy or an aryloxy;

or a salt thereof.

In yet another aspect, the invention comprises a compound of the following structure:

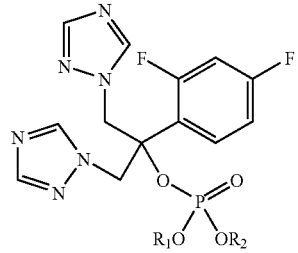

(2)

wherein $R_1$ is H, alkyl, substituted alkyl, aryl or substituted aryl wherein $R_2$ is an alkyl, aryl, alkene, alkyne, a substituted alkene, a substituted alkyl, an alkyl halide, a substituted aryl, a substituted alkyne or an ester substituted six or five member cyclic monosaccharide, or a salt thereof.

In another aspect, the invention comprises a compound of the following structure:

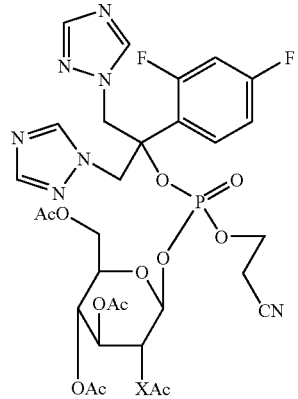

(4)

wherein X is O or NH;
or a salt thereof.

In yet another aspect, the invention comprises a method of synthesizing compound (1) which comprises:
adding a compound of the following formula:

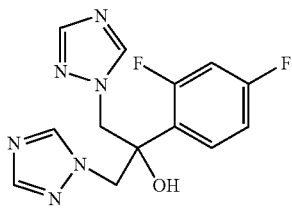
(10)

to a mixture comprised of a solvent to form a reaction mixture; and adding a carbonyl compound of the formula RCOCl wherein R is an alkyl, aryl, alkene, alkyne, a substituted alkene, a substituted alkyl, a substituted aryl, a substituted alkyne, or an alkyl halide, alkoxy or aryloxy;

to the reaction mixture to produce (1).

In another aspect, the invention comprises a method of synthesizing compound (2) wherein $R_1$ of compound (2) is alkyl, substituted alkyl, aryl, or substituted aryl and wherein $R_2$ of compound (2) i s an alkyl, aryl, alkene, alkyne, a substituted alkene, a substituted alkyl, a substituted alkyne, an alkyl halide or a substituted aryl;

which comprises:

reacting a compound of the formula:

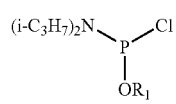
(5)

wherein $R_1$ is an alkyl, substituted alkyl, aryl, or substituted aryl in a first solution comprised of alcohol to form a compound of the formula

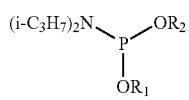
(6)

wherein $R_1$ is alkyl, substituted alkyl, aryl, substituted aryl and wherein $R_2$ is an alkyl, aryl, alkene, alkyne, a substituted alkene, a substituted alkyl, a substituted alkyne, an alkyl halide or a substituted aryl, adding compound (6) to a second solution comprised of a compound of the formula:

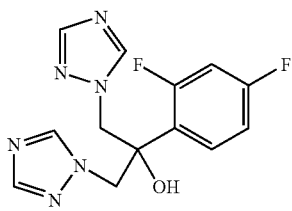
(10)

and an appropriate reagent such as 1-H tetrazole to form a reaction mixture; and adding an oxidating reagent to the reaction mixture to produce compound (2) wherein $R_1$ is alkyl, substituted alkyl, aryl, substituted aryl and wherein $R_2$ is an alkyl, aryl, alkene, alkyne, a substituted alkene, a substituted alkyne, a substituted alkyl, an alkyl halide or a substituted aryl. The $R_1$ is removed by reacting of compound (2) wherein $R_1$ is alkyl, substituted alkyl, aryl, substituted aryl and wherein $R_2$ is an alkyl, aryl, alkene, alkyne, a substituted alkene, a substituted alkyl, a substituted alkyne, an alkyl halide or a substituted aryl with a base to produce a compound (2) wherein wherein $R_1$ is H and $R_2$ is an alkyl, aryl, a substituted alkene, a substituted alkyl, an alkyl halide or a substituted aryl.

In yet another aspect, the invention comprises a method to synthesize a compound of the formula:

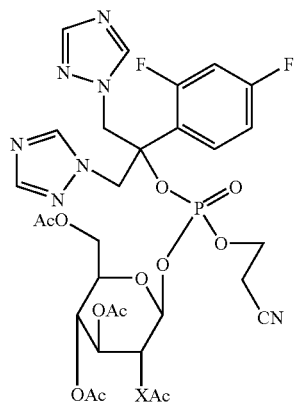
(4)

wherein X=O or NH which comprises:

reacting a compound of the formula:

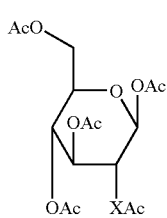
(7)

wherein X is O or NH p0 in a first solution comprised of solvent to produce a compound of the formula:

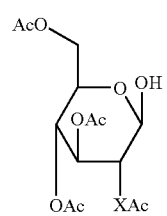
(8)

wherein X is O or NH;

reacting compound (8) in a second solution comprised of a solvent to produce a compound of the formula:

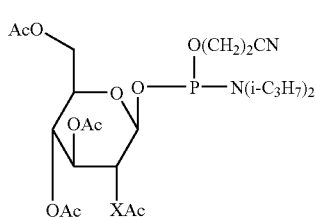

(9)

wherein X=O or NH; and
reacting a compound of the formula:

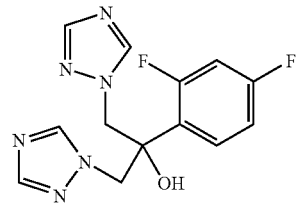

(10)

with compound (9) to produce compound (4).

In another aspect, the invention comprises fluconazole derivatives comprised of the following structure:

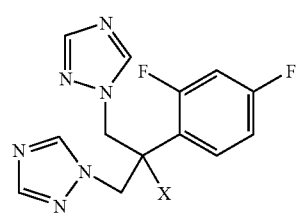

(11)

wherein X is a nitrile, sulfhydryl or halogen, azide, amino, mesyl, tosyl, sulfate, or monosubstituted phosphite or disubstituted phosphite analogs;
or a salt thereof.

In yet another aspect, the invention comprises a method for synthesizing compound (11).

In yet another aspect, the invention comprises derivatives of voriconazole that are believed to exhibit antifungal activity.

In another aspect, the invention comprises carboxylic acid and phosphate ester derivatives of voriconazole that can be used as antifungal agents and methods for synthesizing the same.

In another aspect, the invention comprises a compound of the following structure:

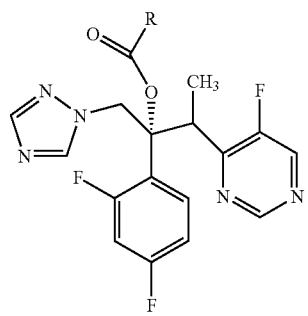

(13)

wherein R is an alkyl, aryl, alkene, alkyne, a substituted alkene, a substituted alkyl, a substituted alkyne, a substituted aryl, an alkyl halide, alkoxy or an aryloxy,
or a salt thereof.

In yet another aspect, the invention comprises a compound of the following structure:

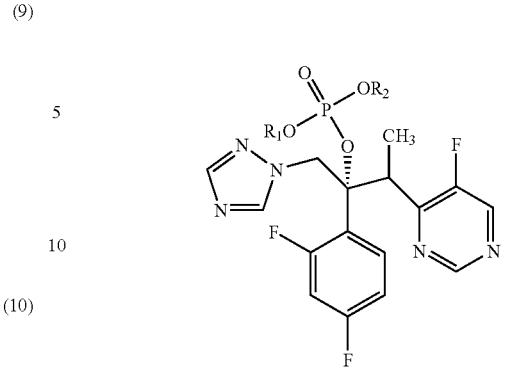

(14)

wherein $R_1$ is H, alkyl, substituted alkyl, aryl or substituted aryl wherein $R_2$ is an alkyl, aryl, alkene, alkyne, a substituted alkene, a substituted alkyl, a substituted alkyne, an alkyl halide, a substituted aryl, alkyne or an ester substituted six or five member cyclic monosaccharide
or a salt thereof.

In yet another aspect, the invention comprises a compound of the following structure:

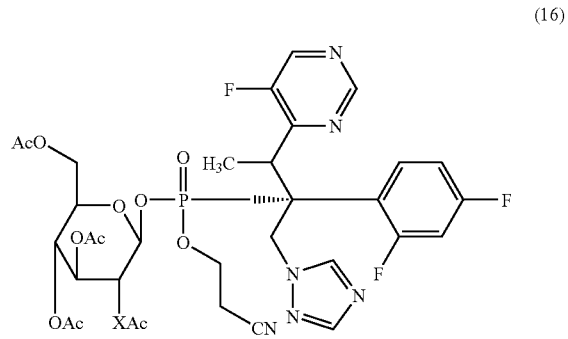

(16)

wherein X is O or NH,
or a salt thereof.

In another aspect, the invention comprises a compound of the following structure:

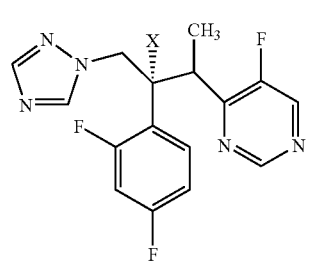

(17)

wherein X is a nitrile, sulfhydryl, halogen, azide, amino, mesyl, tosyl, sulfate, monosubstituted phosphite or disubstituted phosphite analogs,
or a salt thereof.

In another aspect, the invention comprises a pharmaceutical composition comprised of compound (1).

In another aspect, the invention comprises a pharmaceutical composition comprised of compound (2).

In another aspect, the invention comprises a pharmaceutical composition comprised of compound (4).

In another aspect, the invention comprises a pharmaceutical composition comprised of compound (11).

In another aspect, the invention includes a method of treating a human subject suffering from a fungal infection which comprises administering to the subject a therapeutically effective amount of compound (1).

In another aspect, the invention includes a method of treating a human subject suffering from a fungal infection which comprises administering to the subject a therapeutically effective amount of compound (2).

In another aspect, the invention includes a method of treating a human subject suffering from a fungal infection which comprises administering to the subject a therapeutically effective amount of compound (4).

In another aspect, the invention includes a method of treating a human subject suffering from a fungal infection which comprises administering to the subject a therapeutically effective amount of compound (11).

Suitable salts can include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred salt is the sodium salt.

It is to be understood that certain compounds (1), (2), (4) and (11) can exist in solvated as well as unsolvated forms such as, for example, hydrated forms, that invention encompasses all such solvated forms which possess antifungal activity and that the invention relates to all tautomeric forms of compounds (1), (2), (4) and (11) that possess antifungal activity. More particularly, it is to be understood that the invention encompasses all optical, diastereo- and regio-isomers of compounds (1), (2), (4) and (11) that possess antifungal activity.

The pharmaceutical compositions of this invention may be prepared by combining compounds (1), (2), (4) and (11) of the invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier may be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical compositions may be administered to human subjects suffering from fungal infections by employing conventional techniques, e.g., topically or systemically. Systemic routes of administration can include oral, intravenous, intramuscular or subcutaneous injection (including into depots for long-term release), intraocular or retrobulbar, intrathecal, intraperitoneal (e.g. by intraperitoneal lavage), transpulmonary using aerosolized or nebulized drug, or transdermal. Topical routes include administration in the form of ointments, gels, salves, ophthalmic drops or ear drops. The therapeutically effective amount of the active component in the administered pharmaceutical composition may be readily determined by good medical practice and the clinical condition of the human subject being treated.

In yet another aspect, the invention comprises the design of azole derivatives that exhibit antifungal activity. In another aspect, the design of the compounds includes the focus on two targets: 1) the ergosterol biosynthetic pathway and 2) the protein N-myristoyl transferase (NMT).

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
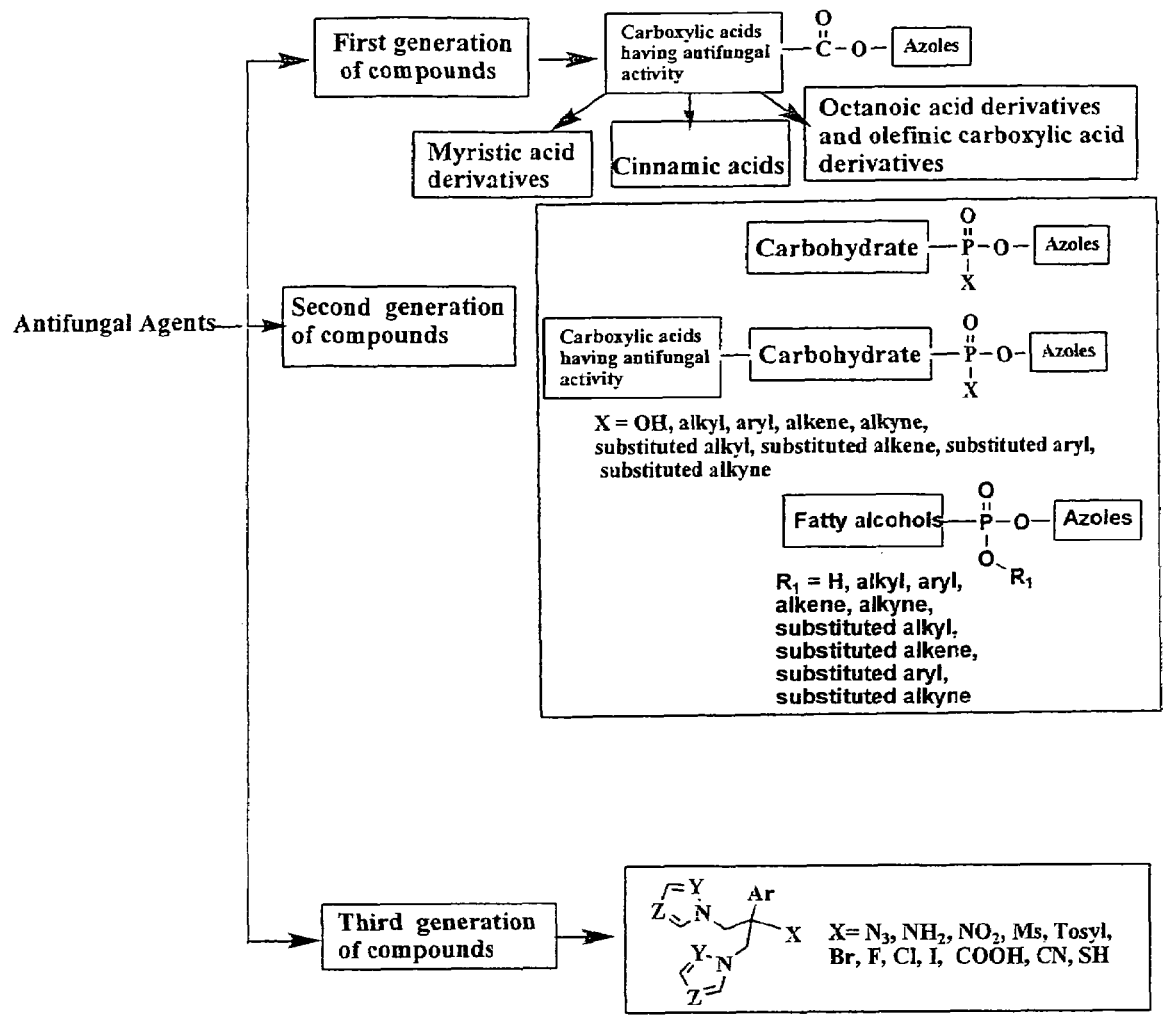
FIG. 1 is a schematic showing designed compounds of the invention.

With reference to FIG. 1, generations of designed compounds are shown. In one embodiment, the design of antifungal compounds of the invention included the focus on two targets: 1) the ergosterol biosynthetic pathway that is inhibited by azole and 2) the protein N-myristoyl transferase (NMT) that is inhibited by myristic acid analogs, respectively. Other mechanisms including cell membrane H+-ATPase may be involved as well.

Azole antifungal agents prevent the synthesis of ergosterol, a major component of fungal plasma membranes, by inhibiting the cytochrome P-450-dependent enzyme lanosterol demethylase (also referred to as 14α-sterol demethylase or $P-450_{DM}$). Georgopapadakou, N. H. et al., *Antimicrob. Agents Chemother.* 1996, 40, 279; Ghannoum, M. A. *Dermatol. Ther.* 1997, 3, 104.

In fungi, a subset of proteins undergoes N-myristoylation involving co-translational transfer of myristate from myristoyl-CoA to the N-terminal glycine of these proteins, in order to affect various diverse biological functions. In fungi, this reaction is catalyzed by NMT, which is inhibited by myristic acid analogs. The NMT enzyme is substrate specific. Peptide substrate specificities are different for mammalian and fugal enzymes and thus may offer a selective target for the designed compounds. Mandala, S. M. et al., *J. Biol. Chem.* 1997, 272, 32709; Parang, K. et al., *Arch. Pharm.-Pharm. Med. Chem.* 1996, 329, 475; VanMiddlesworth, F. et al., *Antibiot. (Tokyo)* 1992, 45, 861; Wang, E. et al., *J. Biol. Chem.* 1991, 266, 14486; Zweerink, M. M. et al., *J. Biol. Chem.* 1992, 267, 25032; Pederson, T. A., *Physiol. Plant (Copenh)* 1970, 23, 654; Nagiec, M. M.; Nagiec, E. E.; Baltisberger, J. A.; Wells, G. B.; Lester, R. L.; Dickson, R. C. *J. Biol. Chem.* 1997, 272, 9809; Langner, C. A.; Travis, J. K.; Caldwell, S. J.; Tianbao, J. E.; Li, Q.; Bryant, M. L.; Devadas, B.; Gokel, G. W.; Kobayashi, G. S.; Gordon, J. I. *J. Biol. Chem.* 1992, 267, 17159.

The designed compounds exhibited antifungal activity and may provide increased drug action, overcome drug resistance, reduced toxicity, increased lipophilicity, increased uptake by fungal cells, increased delivery to the central nervous system, and prolonged plasma half-life. The azole derivatives were designed to target the above-mentioned biochemical machinery in order to inhibit the biochemical pathways in fungi to damage cells and end or control infection. The compounds carry a required agent to affect the aforementioned biochemical machinery and may efficiently reach the infected area due to their pharmacokinetics profile and fungal cell absorption and retention properties.

The design will allow the production of generations of antifungal compounds that may provide the following advantages: 1) both active components of the compounds may be released thereby increasing the efficacy of the compounds 2) the generation of compounds that will include two antifungal agents, a triazole and a fatty acid analog, each agent having different target sites; 3) the generation of compounds that will include two antifungal agents, a triazole and a fatty acid analog, such that the fatty acid analog may be hydrolyzed by cellular esterase that may result in the slow, sustained release of the triazole; 4) the generation of compounds that will include two antifungal agents, a triazole and a fatty acid analog, such that the fatty acid anaolog may increase the compounds lipophilicity; 5) the generation of compounds that include two antifungal agents, an azole and a carbohydrate having fatty acid moieties, such that the carbohydrate is similar in structure to the carbohydrates forming the wall of the fugal cell; and 6) the generation of compounds that include two antifungal agents, an azole and a carbohydrate having fatty acid moieties, joined by a linker, a phosphate, such that the carbohydrate has structure similar to carbohydrates found in pathogenic fungal cells thereby rendering the compounds selective for the fungal cells.

Chemistry

Scheme 1.
Synthesis of carboxylic acid ester derivatives of FLC.

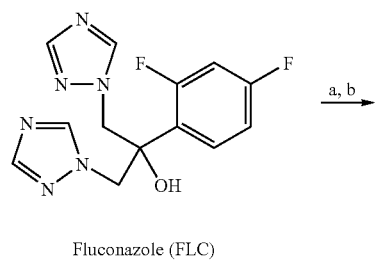

Fluconazole (FLC)

-continued

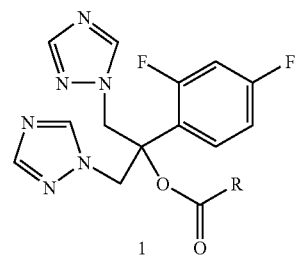

a R = $CH_3^-$
b R = n-$C_{13}H_{27}^-$
c R = $CH_3CH(Br)^-$
d R = $C_2H_5CH(Br)^-$
e R = n-$C_3H_7CH(Br)^-$
f R = n-$C_4H_9CH(Br)^-$
g R = n-$C_6H_{13}CH(Br)^-$
h R = n-$C_{10}H_{21}CH(Br)^-$
i R = n-$C_{12}H_{25}CH(Br)^-$
j R = n-$CH_2(Br)C_9H_{18}^-$
k R = $ClCH_2CH_2O^-$
l R = 2-$OCOCH_3$—$C_6H_4^-$

Reagents and conditions: (a) NaH, DMF, rt, 2 h; (b) RCOCl, rt, 3 h.

Scheme 1 shows the procedure for the preparation of carboxylic acid ester derivatives of FLC (1a-l) from the reaction of acyl chlorides with FLC in the presence of sodium hydride. Acyl chlorides were synthesized from the corresponding carboxylic acids with thionyl chloride in dry benzene if they were not commercially available.

Scheme 2.
Synthesis of alkylphosphate derivatives of FLC.

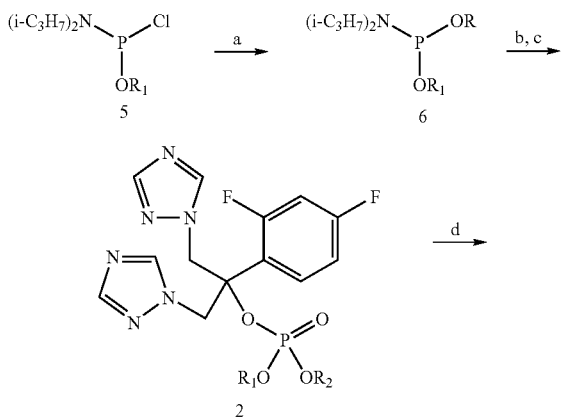

a $R_1$ = $C_2H_4CN$, $R_2$ = n-$C_{11}H_{23}^-$
b $R_1$ = $C_2H_4CN$, $R_2$ = n-$CH_2$=$CHC_9H_{18}^-$
c $R_1$ = $C_2H_4CN$, $R_2$ = n-$BrCH_2C_{10}H_{20}^-$
d $R_1$ = $C_2H_4CN$, $R_2$ = n-$C_{14}H_{29}^-$
e $R_1$ = $C_2H_4CN$, $R_2$ = n-$C_8H_{17}^-$
f $R_1$ = $CH_3^-$, $R_2$ = n-$C_{11}H_{21}^-$
g $R_1$ = $CH_3^-$, $R_2$ = n-$CH_2$=$CHC_9H_{18}^-$
h $R_1$ = $CH_3^-$, $R_2$ = n-$C_8H_{17}$

-continued

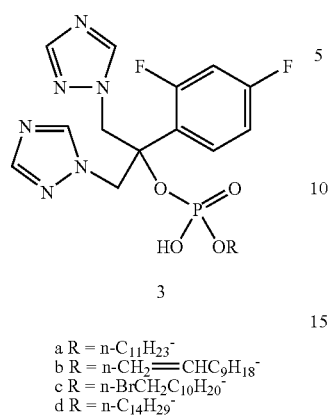

3 a R = n-C$_{11}$H$_{23}$⁻
b R = n-CH$_2$═CHC$_9$H$_{18}$⁻
c R = n-BrCH$_2$C$_{10}$H$_{20}$⁻
d R = n-C$_{14}$H$_{29}$⁻

Reagents and conditions: (a) ROH, DIEA, DCM, rt, 20 h;
(b) FLC, 1H-tetrazole, DCM, 2 h, rt: (c) tBuOOH (28%), 0° C. 1 h; (d) NH$_4$OH/MeOH, 24 h, rt.

Scheme 2 demonstrates the preparation of phosphate triester derivatives of FLC (2a-h). The reaction of alcohol (ROH) with phosphorylating reagents, cyanoethyl N,N-diisopropylchlorophosphoramidite or methyl N,N-diisopropylchlorophosphoramidite (5), in the presence of diisopropyl ethylamine in dry DCM gave N,N-disopropylamine phosphine derivatives (6). Coupling reactions of FLC with 6 in the presence of 1-H-tetrazole in DCM followed by oxidation with t-butyl hydroperoxide afforded phosphate triesters (2a-h). The cyanoethyl protecting group in 2a-d was cleaved using ammonium hydroxide to yield the corresponding phosphate diester derivatives of FLC (3a-d).

Figure 2:
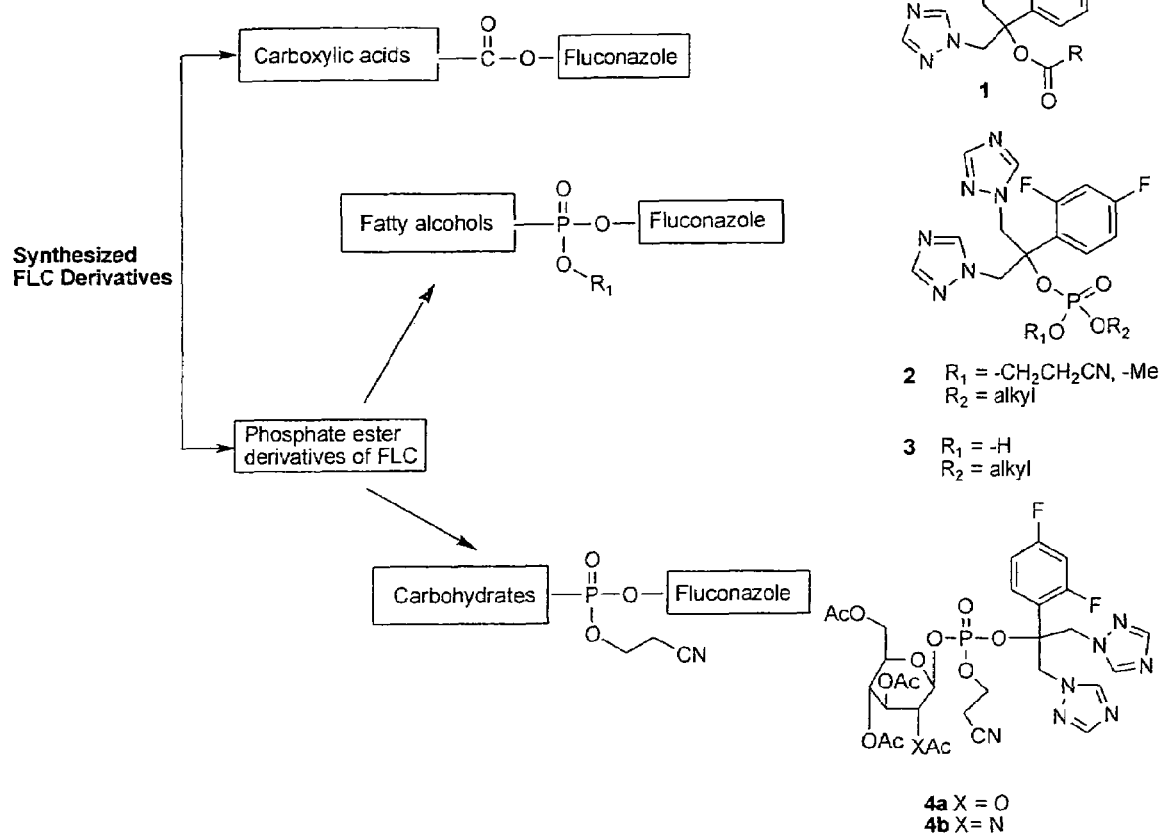
FIG. 2 is a schematic showing two classes of synthesized fluconazole derivatives.

With reference to FIG. 2, two classes of synthesized FLC derivatives are shown.

Scheme 3.
Synthesis of carbohydrate phosphate triester derivatives of FLC.

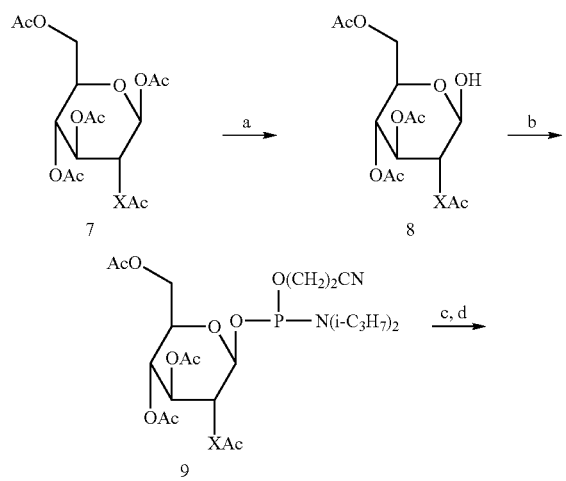

-continued

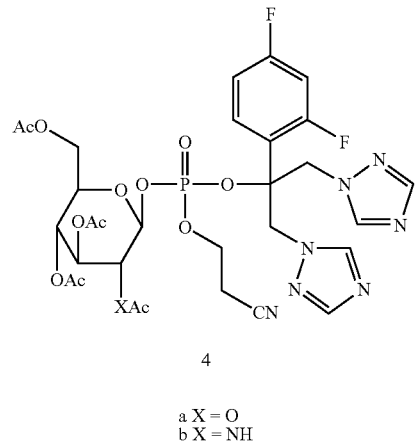

4 a X = O
b X = NH

Reagents and conditions: (a) BnNH$_2$, THF; (b) 2-cyanoethyl N,N-diisopropylchlorophosphoramidite, DIEA, DCM, 20 h;
(c) 1. FLC, 1H-tetrazole, DCM, 2 h, rt; (d) tBuOOH, 0° C., 1 h.

Scheme 3 displays the synthesis of carbohydrate phosphate triester derivatives of FLC (4a and 4b). The reaction of β-D-glucosepentaacetate (7a) or 2-acetamido-2-deoxy-1,3,4,6-tetra-O-acetyl-β-D-glucopyranoside (7b) with benzylamine in THF resulted in the selective removal of the anomeric O-acetyl group to produce the reducing carbohydrates 8a and 8b. Reaction of 8 with cyanoethyl N,N-diisopropylchlorophosphoramidite followed by coupling with FLC and oxidation reaction in the presence of t-butyl hydroperoxide furnished carbohydrate phosphate triesters (4a and 4b).

Antifungal Activity

Biological data for FLC derivatives show that the in vitro antifungal activity is dependent upon the nature of substituent(s) attached to FLC and/or incorporated into the chain of carboxylic acids or fatty alcohols. These groups of compounds exhibited a broad range of antifungal activities.

Carboxylic Acid Ester Derivatives of FLC (1)

The in vitro antifungal test results for carboxylic acid ester derivatives of FLC (1) are presented in Table 1. FLC was active against *C. albicans* in RPMI medium (MIC=2.3 µg/mL), but showed complete resistance against *C. albicans* in SDB medium (MIC≧4,444 µg/mL). All carboxylic acid derivatives of FLC (1a-1l) exhibited lower antifungal activity than FLC in RPMI 1640 growth medium. Two compounds, O-2-bromooctanoylfluconazole (1g) (MIC≦14 µg/mL) and O-11-bromoundecanoylfluconazole (1j, MIC=12 µg/mL) exhibited antifungal activity against *C. albicans* in RPMI and were the most active antifungal agents in this group of compounds against all fungi tested. Since these compounds are carboxylic esters, it was -believed that they could be partially or completely hydrolyzed in vitro, releasing FLC and carboxylic acids. Therefore, the true activity of these compounds may not be determined accurately in vitro RPMI medium with pH=6.9. The half-life for chemical hydrolysis of all 2-bromosubstituted ester derivatives of FLC (1c-1i) was calculated to be approximately 74 days at pH 6.9 using the HYDROWIN (Version 1.67) estimation program. The hydrolysis rate may be slow probably due to the steric hindrance around the esteric functional group, surrounded by three aromatic groups and long chain alkyl chain, sometimes substituted with bulky substituents such as bromine. However, all compounds showed higher antifungal activity than FLC against *C. albicans* in SDB medium (pH=5.6). FLC was completely inactive against *C. albicans* in SDB and thus the antifungal effects of carboxylic ester derivatives of FLC (1a-1l) may not be exclusively due to ester hydrolysis and the release of FLC. Compounds 1g (MIC=111 µg/mL) and 1j (MIC=198 µg/mL) were at least 40 and 22 fold more active against *C. albicans* in SDB, respectively, than that for FLC. Furthermore, compounds 1g (MIC=111 µg/mL) and 1j (MIC=395 µg/mL) were at least 5.2 and 1.5 fold more potent than FLC against *A. niger* indicating the important role of carboxylic acids attached to FLC through ester moiety in enhancing antifungal activity. The antifungal activity of carboxylic ester 1j against *C. neoformans* was comparable to FLC. Although compounds 1g and 1j exhibited 8 and 17 fold less antifungal activity against *C. albicans* in SDB than that in RPMI, respectively, they were still significantly more active than FLC and other analogs in SDB, indicating the presence of an additional mechanism(s) other than ester hydrolysis for antifungal activity of these compounds.

in lipophilicity and the size of the alkyl ester substituent in carboxylic acid ester derivatives of FLC could provide a correlation of antifungal activity with physicochemical properties. All compounds (1a-1l) showed larger estimated partition coefficients (log P=1.26 to 7.42) than that for FLT (log P=0.25). Similarly all carboxylic ester derivatives of FLC (1a-1l) had higher estimated dermal permeability coefficients (Kp) (1.05 to 1,610 µ/hr) than that for FLC (Kp=0.39 µ/hr) indicating the potential for using carboxylic ester analogs for dermal delivery of FLC. Since all carboxylic ester derivatives of FLC are lipophlic, their penetration through the lipid matrix of the stratum corneum of skin and also their penetration into cells might be more efficient. More research is required to confirm this postulation. A relationship between antifungal activity against all fungi tested and the calculated log P for these carboxylic ester derivatives of FLC may exist. There is a correlation in the number of methylene groups and the antifungal activity of 2-bromosubstituted ester derivatives of FLC (1c-1i). As the number of carbon atoms increases, the antifungal activities

TABLE 1

General structure, physicochemical properties and antifungal activity (MIC values, µg/mL)[a] against *Candida albicans* (RPMI and SDB), *Cryptococcus neoformans* (SDB), and *Aspergillus niger* (SDB) at 35-37° C. after 24-48 h and for carboxylic acid ester derivatives of FLC (1).

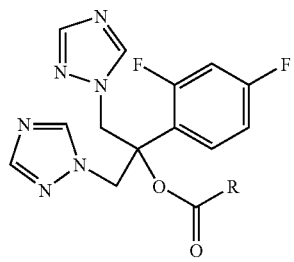

1

| Compound | C. albicans ATCC 14053, RPMI | C. albicans, ATCC 14053, SDB | C. neoformans ATCC 66031, SDB | A. niger ATCC 16404, SDB | Log P[b] | Kp (µ/hr)[c] |
|---|---|---|---|---|---|---|
| 1a | >1,420 | 1,420 | >1,420 | ≧1,420 | 1.26 | 1.12 |
| 1b | 718 | 718 | 718 | ≧718 | 7.15 | 1,610 |
| 1c | 656 | 656 | 656 | >656 | 2.02 | 1.05 |
| 1d | 319 | 636 | >1,276 | ≧1,276 | 2.51 | 1.93 |
| 1e | 275 | 552 | 1,100 | ≧1,100 | 3.00 | 3.54 |
| 1f | 61 | 492 | 492 | ≧979 | 3.49 | 6.49 |
| 1g | ≦14 | 111 | 14 | 111 | 4.48 | 21.80 |
| 1h | 1,466 | 1,466 | 1,466 | ≧1,466 | 6.44 | 246 |
| 1i | 731 | 731 | 731 | >731 | 7.42 | 826 |
| 1j | 12 | 198 | 6.1 | 395 | 6.02 | 151 |
| 1k | 977 | >977 | >977 | >977 | 1.86 | 1.22 |
| 1l | ≧1,212 | >1,212 | >1,212 | >1,212 | 2.31 | 1.16 |
| FLC | 2.3 | ≧4,444 | 2.4 | >580 | 0.25 | 0.39 |
| AMB | 0.7 | 1.5 | <37 | 0.4 | −3.76 | $5.08 \times 10^{-8}$ |
| DMSO | >5,000 | >5,000 | >5,000 | >5,000 | | |

[a]The result is the average of three separate experiments;
[b]Partition coefficient of the compound calculated using the KowWin program;
[c]Dermal permeability coefficient of the compound calculated using the DermWin program (µ/hour).

Estimated partition coefficients (log P), which can be used as an indicator of passive diffusion across cell membranes and cellular uptake, were determined for all carboxylic ester derivatives of FLC (1a-1l). Increasing the length of ester chain or attaching lipophilic substituents such as bromine, affected lipophilicity dramatically (Table 1). The differences are increased up to the maximum level in O-2-bromooctanoylfluconazole (1g). The antifungal activities are then diminished significantly in compounds 1h and 1i, indicating the limit of tolerance for hydrophobicity in generating maximum antifungal activity in this group of compounds. The conjugate ester O-2-bromooctanoylfluconazole (1g) has an estimated log P value of 4.48 that was optimal among 2-bromosubstituted ester derivatives of FLC (1c-1i) for maximum antifungal activity. The highly lipophilic compounds, such as 1h, 1i, exhibited weaker antifungal activity than other analogs. 2-Bromosubstituted ester analogs with shorter chain, such as 1c-1f or carboxylic acid ester derivatives without a bromine group, such as 1k and 1l, generally exhibited weak antifungal activity. Another potent antifungal compound, O-11-bromoundecanoylfluconazole (1j), has a log P value of 6.02 suggesting that additional factors such as the intracellular rate of ester hydrolysis, the stability of ester prior to membrane penetration or in culture medium, and the nature, size, and position of the substituent attached to the chain, may also contribute to overall antifungal effect observed. Differences in the ester hydrolysis are expected to be dependent upon the steric size of the attached acyl group where more sterically hindered esters may possess longer half-lives.

In general 2-bromosubstituted analogs may be more stable than other carboxylic esters as previously shown in 5'-O-myristoyl analog derivatives of zidovudine. Parang, K. et al., *Antiviral. Chem. Chemother.* 1998, 9, 311. Stability of fatty acid derivatives were estimated using HYRDROWIN (Version 1.67) at pH 5.6 used in SDB medium indicating high stability of these compounds probably due to the presence of tertiary esteric functional group surrounded by bulky aromatic and nonaromatic groups. For example the estimated half-life for all 2-bromosubstituted carboxylic acid esters at pH 5.6 is approximately 4 years. Therefore, chemical hydrolysis may not contribute significantly to release of components. However, esters may be hydrolyzed in vitro by the action of fungal esterases.

Carboxylic Acid and Fatty Alcohol Derivatives

The in vitro antifungal results for several carboxylic acids and fatty alcohols are presented in Table 2. In general, fatty alcohols showed significantly higher antifungal activities against *C. neoformans* and *A. niger* than those of the corresponding fatty acids. For example, tetradecanol (MIC=14 µg/mL) and 11-bromoundecanol (MIC=12 µg/mL) were more potent than tetradecanoic acid (MIC>529 µg/mL) and 11-bromoundecanoic acid (MIC=23 µg/mL), against *C. neoformans* in SDB, respectively. The antifungal activities of primary aliphatic alcohols from $C_6$ to $C_{13}$ have been previously reported against *Saccharomyces cerevisae*. Kubo, I. et al., *Bioorg. Med. Chem.* 2003, 11, 1117.

It is believed that the primary mechanism for the antifungal action of alkanols is due to their amphipathic characteristics and ability as nonionic surfactants to disrupt the native membrane-associated function of the integral proteins. Kubo, I. et al., *Bioorg Med. Chem.* 2003, 11, 1117. The higher antifungal activity of fatty alcohols compared to the corresponding carboxylic acids with similar chain length is not known, but may be due to their better surfactant effect or other mechanism(s) of antifungal action.

TABLE 2

Physicochemical properties and antifungal activity (MIC values, µg/mL)[a] against *Candida albicans* (RPMI and SDB), *Cryptococcus neoformans* (SDB), and *Aspergillus niger* (SDB) at 35-37° C. after 24-48 h and for carboxylic acid and fatty alcohols.

| Compound | MIC (µg/mL) | | | | Log P[b] | Kp (µ/hr)[c] |
| --- | --- | --- | --- | --- | --- | --- |
| | C. albicans ATCC 14053, RPMI | C. albicans, ATCC 14053, SDB | C. neoformans ATCC 66031, SDB | A. niger ATCC 16404, SDB | | |
| Acetic acid | ≧220 | ≧220 | ≧220 | ≧220 | 0.09[d] | 6.21 |
| 2-Bromopropionyl chloride | 468 | 468 | 117 | 468 | 0.29 | 2.75 |
| 2-Bromobutyric acid | 513 | >513 | >513 | ND[e] | 1.34[f] | 18.60 |
| 2-Bromovaleric acid | ≧578 | 578 | 290 | ≧578 | 1.83 | 29.90 |
| 2-Bromohexanoic acid | ≧710 | 710 | 355 | 710 | 2.32 | 54.70 |
| 2-Bromooctanoic acid | 865 | 865 | 433 | ND | 3.30 | 184 |
| 2-Bromolauric acid | 155 | 155 | 19 | 78 | 5.27 | 2,070 |
| 2-Bromomyristic acid | 12 | >540 | 15 | 68 | 6.25 | 6,970 |
| 11-Bromoundecanoic acid | 371 | 185 | 23 | 93 | 4.85 | 1,280 |
| Decanoic acid | 791 | 99 | ND | <12 | 4.02[g] | 1,360 |
| Tetradecanoic acid | >876 | 1,750 | >529 | >529 | 5.98[h] | 16,800 |
| 1-Undecanol | ND | 87 | 28 | 87 | 4.28 | 1,850 |
| ω-Undecylenyl alcohol | ND | 110 | 14 | 27 | 4.14 | 1,520 |
| Tetradecanol | ND | 1,720 | 14 | 27 | 5.75[i] | 17,900 |
| 11-Bromoundecanol | ND | 95 | 12 | 24 | 4.62 | 1,070 |
| FLC | 2.3 | ≧4,444 | 2.4 | >580 | 0.25 | 0.39 |
| AMB | 0.7 | 1.5 | <3.7 | 0.4 | −3.76 | 5.08 × 10$^{-8}$ |
| DMSO | >5,000 | >5,000 | >5,000 | >5,000 | | |

[a]The result is the average of three separate experiments;
[b]Partition coefficient of the compound calculated using the KowWin program;
[c]Dermal permeability coefficient of the compound calculated using the DermWin program (µ/hour);
[d]Experimental log P = −0.17;[52]
[e]ND = Not determined;
[f]Experimental log P = 1.42;[52]
[g]Experimental log P = 4.09;[52]
[h]Experimental log P = 6.11;[53]
[i]Experimental log P = 6.03.[54]

All carboxylic acids were equally active against *C. albicans* in SDB and RPMI media with the exception of 2-bromomyristic acid and 11-bromoundecanoic acid which showed higher and lower antifungal activity in RPMI, respectively, than that in SDB. 2-Bromolauric, 2-bromomyristic, and 11-bromoundecanoic acids were found to be the most active antifungal agents in this group of carboxylic acids against all fungi tested. 11-Bromoundecanoic acid showed comparable activity to 2-bromolauric acid against all three fungi tested in SDB medium. The antifungal activity of 2-bromomyristic acid and 11-bromoundecanoic acid against C. albicans in RPMI medium was in agreement with reported results. Parang, K., Knaus, E. E.; Wiebe, L. I.; Sardari, S.; Daneshtalab, M.; Csizmadia, F. Arch. Pharm.-Pharm. Med. Chem. 1996, 329, 475. A relationship between antifungal activity against all fungi tested and the calculated log P for 2-bromosubstituted analogs may exist. A log P value in the range of 5.3-6.3 is required for the broad spectrum antifungal activity against fungi tested in SDB medium. 2-Bromosubstituted analogs with shorter chain fatty acids or carboxylic acids without a bromine group generally exhibited weak antifungal activity. Thus, the hydrophobicity in the activity of fatty acid derivatives may be important. The cutoff in the observed antifungal activity may be due to a corresponding limit in the absorption of carboxylic acids into lipid-bilayer portions of membranes. Shorter chain carboxylic acids may enter the cell by passive diffusion across plasma membrane and do not incorporate into the cell membrane. Longer chain and non-brominated carboxylic acids may be soluble in the membrane phospholipids, and therefore may be incorporated into hydrophobic domain of the membrane. Amphipathic medium-chain carboxylic acids may act as surfactants. All carboxylic acids and fatty alcohols had higher estimated dermal permeability coefficient (Kp=2.75 to 17,900 μ/hr) than FLC (Kp=0.39 μ/hr).

Phosphate Ester Derivatives of FLC (2-4)

Based on the antifungal activity data for compounds in Table 2, the fatty alcohols were selected for further preparation of phosphate diester and triester derivatives of FLC. The in vitro antifungal test results for the fatty alcohol phosphate triester (2a-2h) and diester (3a-3d) derivatives of FLC are presented in Table 3. In general, in comparison to FLC, this group of compounds had increased activity against C. albicans in SDB medium in which FLC was inactive indicating the importance of fatty alcohol portion and phosphate linker in enhancing antifungal activities. FLC phosphate triesters of FLC (2) were more potent antifungal agents than phosphate diesters (3). Compounds 2a, 2b and 2g were the most potent antifungal agents in this group against C. albicans in SDB medium. Compounds 2a, 2c, and 2f were found to be potent antifungal agents against C. neoformans (MIC=12 to 31 μg/mL). Compound 2f with a MIC value of 190 μg/mL was the most potent compound tested in this group against A. niger. Factors important to the in vitro antifungal activity for these compounds may include: (i) the intrinsic activity of the intact ester derivative; (ii) the rate and extent of cellular uptake; and/or (iii) the rate and extent at which the two substrate moieties FLC and the fatty alcohol analog are released following hydrolysis of the conjugate ester. The mechanism of intrinsic activity of these derivatives may be due to their amphipathic structure. Hydrophilic parts of the molecule such as protonated triazoles may bind with the hydrophilic portion of fungal cell membrane, while the hydrophobic tail may enter into the membrane lipid bilayer of the membrane. Furthermore, other mechanisms such as hydrolysis of the molecule to FLC and fatty alcohols which have different mechanisms of antifungal action may be involved. All compounds in this group had higher estimated partition coefficients (log P=3.24 to 6.61) and dermal permeability coefficient (Kp=1.63 to 264 μ/hr) than those for FLC (log P=0.25; Kp=0.39 μ/hr).

TABLE 3

General structure, physicochemical properties and antifungal activity (MIC values, μg/mL)[a] against Candida albicans, Cryptococcus neoformans, and Aspergillus niger in SDB at 35-37° C. after 24-48 h and for fatty alcohol phosphate diester (3) and triester (2) derivatives of FLC and controls.

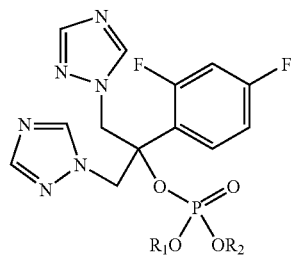

| Compound | $R_1$ | $R_2$ | C. albicans, ATCC 14053 | C. neoformans ATCC 66031 | A. niger ATCC 16404 | Log P[b] | Kp (μ/hr)[c] |
|---|---|---|---|---|---|---|---|
| 2a | CNCH$_2$CH$_2$— | n-C$_{11}$H$_{23}$— | 185 | 23 | 740 | 4.71 | 10 |
| 2b | CNCH$_2$CH$_2$— | n-CH$_2$=CH-C$_9$H$_{18}$— | 122 | 31 | 980 | 4.57 | 8.27 |
| 2c | CNCH$_2$CH$_2$— | n-BrCH$_2$C$_{10}$H$_{20}$— | 1,658 | 26 | 1,658 | 5.05 | 5.82 |
| 2d | CNCH$_2$CH$_2$— | n-C$_{14}$H$_{29}$— | 940 | 235 | 940 | 6.18 | 61.9 |
| 2e | CNCH$_2$CH$_2$— | n-C$_8$H$_{17}$— | 680 | 170 | 1,360 | 3.24 | 1.63 |
| 2f | CH$_3$— | n-C$_{11}$H$_{23}$— | 762 | 12 | 190 | 5.20 | 38.5 |
| 2g | CH$_3$— | n-CH$_2$=CH—C$_9$H$_{18}$— | 228 | 29 | 1,825 | 5.06 | 31.7 |
| 2h | CH$_3$ | n-C$_8$H$_{17}$— | 470 | 59 | 470 | 3.72 | 6.26 |
| 3a | H | n-C$_{11}$H$_{23}$— | 760 | 95 | 760 | 5.14 | 42.8 |
| 3b | H | n-CH$_2$=CH—C$_9$H$_{18}$— | 1,501 | 1,501 | 1,501 | 5.00 | 35.2 |
| 3c | H | n-BrCH$_2$C$_{10}$H$_{20}$— | 1,477 | 185 | 1,477 | 5.48 | 24.8 |
| 3d | H | n-C$_{14}$H$_{29}$— | 940 | 235 | 940 | 6.61 | 264 |

TABLE 3-continued

General structure, physicochemical properties and antifungal activity (MIC values, μg/mL)[a] against
*Candida albicans, Cryptococcus neoformans,* and *Aspergillus niger* in SDB at 35-37° C. after
24-48 h and for fatty alcohol phosphate diester (3) and triester (2) derivatives of FLC and controls.

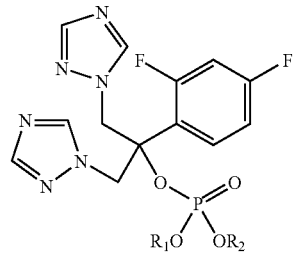

| Compound | R₁ | R₂ | C. albicans, ATCC 14053 | C. neoformans ATCC 66031 | A. niger ATCC 16404 | Log P[b] | Kp (μ/hr)[c] |
|---|---|---|---|---|---|---|---|
| FLC |  |  | ≧4,444 | 2.4 | >580 | 0.25 | 0.39 |
| AMB |  |  | 1.5 | <3.7 | 0.4 | −3.76 | 5.08 × 10⁻⁸ |
| DMSO |  |  | >5,000 | >5,000 | >5,000 |  |  |

[a]The result is the average of three separate experiments;
[b]Partition coefficient of the compound calculated using the KowWin program;
[c]Dermal permeability coefficient of the compound calculated using the DermWin program (μ/hour).

To understand the importance of fatty alcohols in the antifungal activity, fatty alcohols were replaced with carbohydrates. Table 4 shows the antifungal activities for carbohydrate phosphate triester derivatives of FLC (4). The removal of fatty alcohols in the conjugate and substitution with carbohydrates decreased the antifungal activities significantly against all fungi tested. Compounds 4a (log P=−1.32) and 4b (log P=−0.79) showed lower estimated partition coefficients than that for FLC (log P=0.25). The data indicates the important role of fatty alcohols in antifungal activity of phosphate triester and diester derivatives of FLC.

TABLE 4

General structure, Physicochemical properties and antifungal activity
(MIC values, μ/mL)[a] against *Candida albicans, Cryptococcus neoformans,* and-
*Aspergillus niger* in SDB at 35-37° C. after 24-48 h and for carbohydrate phosphate
triester derivatives of FLC (4) and controls.

| Compound | C. albicans ATCC 14053 | C. neoformans ATCC 66031 | A. niger ATCC 16404 | Log P[b] | Kp (μ/hr)[c] |
|---|---|---|---|---|---|
| 4a | 1,999 | 551 | 1,999 | −1.32 | 4.44 × 10⁻⁵ |
| 4b | >3,399 | 306 | 1,699 | −0.79 | 1.07 × 10⁻⁴ |
| FLC | ≧4,444 | 2.4 | >580 | 0.25 | 0.39 |
| AMB | 1.5 | <3.7 | 0.4 | −3.76 | 5.08 × 10⁻⁸ |
| DMSO | >5,000 | >5,000 | >5,000 |  |  |

[a]The result is the average of three separate experiments;
[b]Partition coefficient of the compound calculated using the KowWin program;
[c]Dermal permeability coefficient of the compound calculated using the DermWin program (μ/hour).

Interaction Studies

Figure 3A:
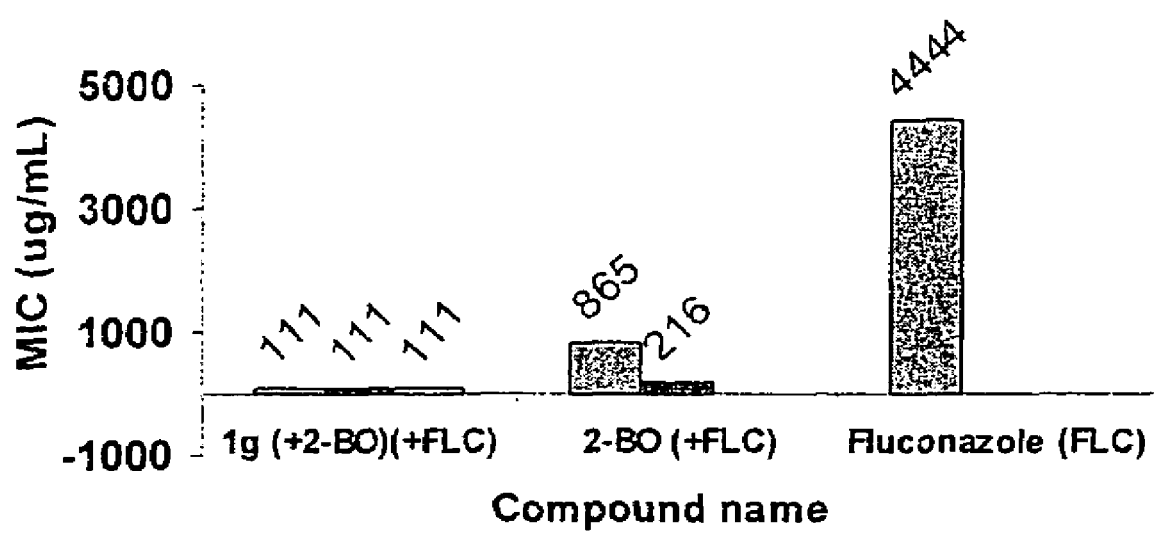
FIG. 3a is a graph comparing the effectiveness of the fluconazole derivatives of the invention to fluconazole against C. albicans ATCC 14053 (SDB)
Figure 3B:
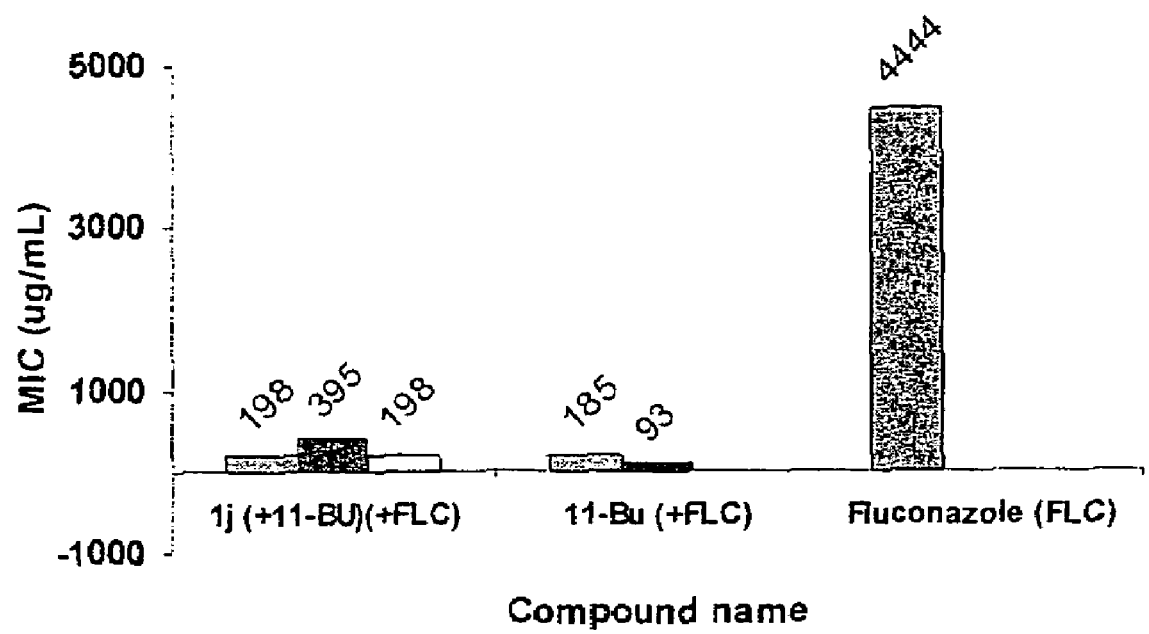
FIG. 3b is another graph comparing the effectiveness of fluconazole derivatives of the invention to fluconazole against C. albicans ATCC 14053 (SDB).

Studies were carried out to determine interactions betweens compounds 1g and 1j against *C. albicans* in SDB growth medium, in which FLC was inactive (FIGS. 3a and 3b). Fractional Inhibitory Concentration (FIC) index [$FIC_{index}=FIC_A+FIC_B$] calculation was used to determine synergism between different components of the synthesized compounds while administered separately, where $FIC_A$ or $FIC_B$ equals to MIC of compounds A or B in combination divided by MIC of drug A or B alone. If the FIC index is $\leq 0.5$, the combination is synergistic. If the FIC value is equal to 1, the combination is additive or "indifferent" and if greater than 4.0, the combination is antagonistic.

While FLC did not show inhibition against *C. albicans* at the highest tested concentration (4,444 µg/mL), the mixture of FLC and 2-BO showed antifungal activity (FIG. 3a). FIC index values for a mixture of 2-bromooctanoic acid (2-BO) and FLC (FIC index=0.30) indicated a synergism effect between these two componenets when mixed. There was no synergistic effect when 1g was mixed with FLC (FIC index=1.05). The presence of FLC and/or 2-BO did not affect the inhibition level of 1g. A mixture of 2-BO and FLC had approximately 2 fold less antifungal inhibition than when 1g used alone or mixed with any of the components (2-BO or FLC). The inequality in the MIC values of the mixed components and the corresponding conjugate ester 1g may be due to differences in cell penetration and disposition of individual components compared with the ester derivative of FLC. Referring to FIGS. 3a and 3b, the results of the interaction study of FLC, 2-broniooctanoic acid (2-Bu), 11-bromoundecanoic acid (11-Bu) with the conjugate ester antifungal agents, 1g and 1j, respectively, against *C. albicans* ATCC 14053 (SDB) is shown.

Some differences were observed in the interaction studies using 11-bromoundecanoic acid (11-Bu) and 1j (FIG. 3b). The mixture of 11-Bu with FLC showed synergistic effect (FIC index=0.52) and fungal inhibitory effect that was approximately equal to that of 1j. While the presence of FLC did not affect the antifungal activity of 1j against *C. albicans* in SDB (FIC index=1.04), addition of 11-Bu reduced the activity of 1j. The lack of interaction of the designed conjugate esters, 1j and 1g, with their individual components (FLC and carboxylic acids), indicate that the ester analogs may have some intrinsic antifungal activity in addition to that of their hydrolysis products, FLC and carboxylic acids, in the site of action.

Experimental (i) General. All products were homogenous by thin-layer chromatography (TLC), performed on Whatman® 250 µm Silica Gel GF Uniplates and visualized under Uv light at 254 nm. Melting points were determined with an electrothermal melting point apparatus and are uncorrected. Chromatographic purification was done by the open flash silica gel column chromatography using Merck silica gel 60 (240 to 400 mesh). Nuclear magnetic resonance spectra ($^1$H NMR) were recorded using tetramethylsilane as an internal standard on a Bruker 400 MHz spectrometer with $CDCl_3$ as a solvent unless otherwise indicated. Chemical shifts are reported in parts per millions (ppm) downfield from tetramethylsilane as an internal standard. Electrospray ionization (ESI) and high-resolution mass spectra were obtained using PE Biosystems API 2000 and Mariner® mass spectrometers, respectively. Reagents and solvents were purchased from Aldrich or Fluka Chemical Corp. (Milwaukee, Wis., USA) unless noted otherwise. Solvents were distilled and dried before use.

(ii) General procedure for the synthesis of carboxylic acid ester derivatives of FLC (1a-h). Dry dimethyl formamide (DMF) (2 mL) was added to sodium hydride (48 mg, 40% immersion in oil, 1.2 mmol, prewashed with dry hexane) and the mixture was cooled to 0° C. A solution of FLC (300 mg, 1 mmol) in dry DMF was slowly added to this mixture. After stirring for 2 h at room temperature, the reaction mixture was cooled down again in an ice bath; thereafter a solution of acyl chloride (1.5 mmol, freshly prepared by refluxing the corresponding carboxylic acid with thionyl chloride if not commercially available) in dry benzene was added dropwise during 30 min. The reaction mixture was stirred for a further period of 3 h at room temperature and poured into a separatory funnel containing cold aqueous sodium bicarbonate (5%, 100 mL). The crude product was extracted with ethyl acetate (EA) (2×100 mL). The organic layers were combined, dried over magnesium sulfate ($MgSO_4$), and concentrated in vacuo. The residue, which consisted of one major product, was purified by a silica gel column chromatography using hexane/acetone (3:1 v/v to 1:1 v/v) as eluting solvents to yield final products (Scheme 1).

O-Acetylfluconazole (1a). The general synthetic method described above afforded 1 a (78.0%) as an amorphous powder; mp. 131.5-133.1° C.; $^1$H NMR ($CDCl_3$, 400 MHz) δ 7.97 (2H, s), 7.88 (2H, s), 6.90-6.74 (3H, m), 5.14 (2H, d, J=14.5 Hz), 5.05 (2H, d, J=14.5 Hz), 2.15 (3H, s). HR-MS (ESI-TOF) calculated for $C_{16}H_{16}F_2N_6O_2$ 348.1146, found 349.1222 (M+H). ESI m/z 349.2 (M+H), 220.2 (M-$C_4H_5N_3O_2$).

O-Tetradecanoylfluconazole (1b). The general synthetic method described above afforded 1b (67.0%) as an amorphous powder; mp. 142-143° C.; $^1$H NMR ($CDCl_3$, 400 MHz) δ 7.95 (2H, s), 7.84 (2H, s), 6.88-6.75 (3H, m), 5.15 (2H, d, J=15.3 Hz), 5.50 (2H, d, J=15.3 Hz), 2.37 (2H, t, J=7.5 Hz), 1.54-1.22 (22H, m, methylene envelope), 0.99 (3H, t, J=8.2 Hz). HR-MS (ESI-TOF) calculated for $C_{28}H_{40}F_2N_6O_2$ 516.3024, found 517.3057 (M+H). ESI m/z 517.3 (M+H), 220.1 (M-$C_{16}H_{29}N_3O_2$).

O-2-Bromopropionylfluconazole (1c). The general synthetic method described above afforded 1c (38.0%) as a syrup; $^1$H NMR ($CDCl_3$, 400 MHz) δ 8.20 (2H, s), 7.90 (2H, s), 7.08 (1H, d, J=8.1 Hz), 7.00 (1H, d, J=2.2 Hz), 6.80 (1H, dd, J=8.1 Hz, 2.2 Hz), 5.39 (2H, d, J=15.0 Hz), 5.20 (2H, d, J=15.0 Hz), 4.45 (1H, q, J=7.5 Hz), 1.83 (3H, d, J=7.5 Hz). HR-MS (ESI-TOF) calculated for $C_{16}H_{15}BrF_2N_6O_2$ 440.0408, found 441.0411 (M+H, $^{79}$Br), 443.1416 (M+H, $^{81}$Br). ESI m/z 441.1 (M+H, $^{79}$Br), 443.1 (M+H, $^{81}$Br), 372.0 (M-$C_2H_2N_3$, $^{79}$Br), 374.0 (M-$C_2H_2N_3$, $^{81}$Br), 289.3 (M-$C_3H_4BrO_2$), 220.1 (M-$C_5H_6BrN_3O_2$).

O-2-Bromobutyrylfluconazole (1d). The general synthetic method described above afforded 1d (31.0%) as a syrup; $^1$H NMR ($CDCl_3$, 400 MHz) δ 8.20 (2H, s), 7.99 (2H, s), 7.10 (1H, d, J=8.5 Hz), 7.05 (1H, d, J=2.1 Hz), 6.88 (1H, dd, J=8.5 Hz, 2.1 Hz), 5.39 (2H, d, J=13.4 Hz), 5.15 (2H, d, J=13.4 Hz), 4.30 (1H, t, J=7.5 Hz), 1.49-1.40 (2H, m), 1.15 (3H, t, J=8.2 Hz). HR-MS (ESI-TOF) calculated for $C_{17}H_{17}BrF_2N_6O_2$ 454.0564, found 455.0531 (M+H, $^{79}$Br), 457.0542 (M+H, $^{81}$Br). ESI m/z 455.3 (M+H, $^{79}$Br), 457.3 (M+H, $^{81}$Br), 386.1 (M-$C_2H_2N_3$, $^{79}$Br), 388.1 (M-$C_2H_2N_3$, $^{81}$Br), 289.3 (M-$C_4H_6BrO_2$), 220.1 (M-$C_8H_8BrN_3O_2$).

O-2-Bromovaleroylfluconazole (1e). The general synthetic method described above afforded 1e (55.0%) as a syrup; $^1$H NMR (CDCl$_3$, 400 MHz) δ 8.22 (2H, s), 8.00 (2H, s), 7.15 (1H, d, J=8.3 Hz), 7.09-6.80 (2H, m), 5.40 (2H, d, J=16.1 Hz), 5.12 (2H, d, J=16.1 Hz), 4.38 (1H, t, J=7.2 Hz), 2.12-2.00 (2H, m), 1.49-1.42 (2H, m), 0.96 (3H, t, J=7.5 Hz). HR-MS (ESI-TOF) calculated for $C_{18}H_{19}BrF_2N_6O_2$ 468.0721, found 469.0712 (M+H, $^{79}$Br), 471.0711 (M+H, $^{81}$Br). ESI m/z 469.0 (M+H, $^{79}$Br), 471.1 (M+H, $^{81}$Br), 400.0 (M-$C_2H_2N_3$, $^{79}$Br), 402.1 (M-$C_2H_2N_3$, $^{81}$Br), 289.3 (M-$C_5H_8BrO_2$), 220.1 (M-$C_7H_{10}BrN_3O_2$).

O-2-Bromohexanoylfluconazole (1f). The general synthetic method described above afforded 1f (69.0%) as a syrup; $^1$H NMR (CDCl$_3$, 400 MHz) δ 8.16 (2H, s), 7.98 (2H, s), 7.09 (1H, d, J=8.3 Hz), 6.88 (1H, d, J=2.5 Hz), 6.79 (1H, dd, J=8.3 Hz, 2.5 Hz), 5.38 (2H, d, J=14.2 Hz), 5.11 (2H, d, J=14.2 Hz), 4.41 (1H, t, J=7.7 Hz), 2.05-1.85 (2H, m), 1.33-1.20 (4H, m, methylene envelope), 0.99 (3H, t, J=7.1 Hz). HR-MS (ESI-TOF) calculated for $C_{19}H_{21}BrF_2N_6O_2$ 482.0877, found 483.0711 (M+H, $^{79}$Br), 485.1021 (M+H, $^{81}$Br). ESI m/z 483.0 (M+H, $^{79}$Br), 485.1 (M+H, $^{81}$Br), 414.0 (M-$C_2H_2N_3$, $^{79}$Br), 416.1 (M-$C_2H_2N_3$, $^{81}$Br), 289.3 (M-$C_6H_{10}BrO_2$), 220.1 (M-$C_8H_{12}BrN_3O_2$).

O-2-Bromooctanoylfluconazole (1g). The general synthetic method described above afforded 1g (75.0%) as a syrup; $^1$H NMR (CDCl$_3$, 400 MHz) δ 8.20 (2H, s), 7.82 (2H, s), 7.05 (1H, d, J=8.8 Hz), 6.92 (1H, d, J=2.7Hz), 6.80 (1H, dd, J=8.8 Hz, 2.7 Hz), 5.39 (2H, d, J=15.1 Hz), 5.09 (2H, d, J=15.1 Hz), 4.31 (1H, t, J=7.7 Hz), 2.05-1.99 (2H, m), 1.59-1.32 (8H, m, methylene envelope), 0.90 (3H, m). HR-MS (ESI-TOF) calculated for $C_{21}H_{25}BrF_2N_6O_2$ 510.1190, found 511.2011 (M+H, $^{79}$Br), 513.3101 (M+H, $^{81}$Br), ESI m/z 511.2 (M+H, $^{79}$Br), 513.3 (M+H, $^{81}$Br), 289.3 (M-$C_{10}H_{16}Bro_2$), 220.1 (M-$C_8H_{12}BrN_3O_2$).

O-2-Bromolauroylfluconazole (1h). The general synthetic method described above afforded 1h (91.0%) as a syrup; $^1$H NMR (CDCl$_3$, 400 MHz) δ 8.19 (2H, s), 7.90 (2H, s), 7.08 (1H, d, J=8.1 Hz), 6.88 (1H, d, J=2.4 Hz), 6.77 (1H, dd, J=8.1 Hz, 2.4 Hz), 5.32 (2H, d, J=13.7 Hz), 5.07 (2H, d, J=13.7 Hz), 4.28 (1H, t, J=7.5 Hz), 2.13-1.98 (2H, m), 1.59-1.32 (16H, m, methylene envelope), 0.94 (3H, m). HR-MS (ESI-TOF) calculated for $C_{25}H_{33}BrF_2N_6O_2$ 566.1816, found 567.1823 (M+H, $^{79}$Br), 569.1821 (M+H, $^{81}$Br). ESI m/z 567.3 (M+H, $^{79}$Br), 569.4 (M+H, $^{81}$Br), 498.3 (M-$C_2H_2N_3$, $^{79}$Br), 500.3 (M-$C_2H_2N_3$, $^{81}$Br), 289.3 (M-$C_{12}H_{22}BrO_2$), 220.1 (M-$C_{14}H_{24}BrN_3O_2$).

O-2-Bromomyristoylfluconazole (1i). The general synthetic method described above afforded 1i (95.0%) as a syrup; $^1$H NMR (CDCl$_3$, 400 MHz) δ 8.59 (2H, s), 7.88 (2H, s), 7.02 (1H, d, J=8.4 Hz), 6.92 (1H, d, J=2.3 Hz), 6.81 (1H, dd, J=8.4Hz, 2.3 Hz), 5.34 (2H, d, J=14.6 Hz), 5.07 (2H, d, J=14.6 Hz), 4.31 (1H, t, J=7.5 Hz), 2.15-1.97 (2H, m), 1.60-1.21 (20H, m, methylene envelope), 0.95 (3H, m). HR-MS (ESI-TOF) calculated for $C_{27}H_{37}BrF_2N_6O_2$ 594.2129, found 595.2121 (M+H, $^{79}$Br), 597.2132 (M+H, $^{81}$Br). ESI m/z 595.3 (M+H, $^{79}$Br), 597.2 (M+H, $^{81}$Br), 526.3 (M-$C_2H_2N_3$, $^{79}$Br), 528.3 (M-$C_2H_2N_3$, $^{81}$Br), 289.4 (M-$C_{14}H_{26}BrO_2$), 220.1 (M-$Cl_6H_{28}BrN_3O_2$).

O-11-Bromoundecanoylfluconazole (1j). The general synthetic method described above afforded 1j (88.0%) as a syrup; $^1$H NMR (CDCl$_3$, 400 MHz) δ 7.95 (2H, s), 7.85 (2H, s), 6.95-6.88 (1H, m), 6.87-6.71 (2H, m), 5.20 (2H, d, J=15.5 Hz), 5.03 (2H, d, J=15.5 Hz), 3.40 (2H, —CH$_2$Br, t, J=7.7 Hz), 2.32 (2H, COCH$_2$—, t, J=7.7 Hz), 1.90-1.81 (2H, —CH$_2$CH$_2$Br, m), 1.61-1.51 (2H, COCH$_2$CH$_2$—, m), 1.45-1.20 (12H, m, methylene envelope). HR-MS (ESI-TOF) calculated for $C_{24}H_{31}BrF_2N_6O_2$ 552.1660, found 553.1647 (M+H, $^{79}$Br), 555.2111 (M+H, $^{81}$Br). ESI m/z 553.4 (M+H, $^{79}$Br), 555.2 (M+H, $^{81}$Br), 484.2 (M-$C_2H_2N_3$, $^{79}$Br), 486.2 (M-$C_2H_2N_3$, $^{81}$Br), 289.3 (M-$C_{11}H_{20}BrO_2$), 220.1 (M-$C_{13}H_{22}BrN_3O_2$).

O-2-Chloroethyloxycarbonylfluconazole (1k). The general synthetic method described above afforded 1k (75.0%) as a syrup; $^1$H NMR (CDCl$_3$, 400 MHz) δ 8.05 (2H, s), 7.95 (2H, s), 7.05-6.90 (2H, m), 6.88-6.80 (1H, m), 5.15 (2H, d, J=14.3 Hz), 5.05 (2H, d, J=14.3 Hz), 4.50 (2H, —OCH$_2$—, t, J=9.2 Hz), 3.76 (2H, —OCH$_2$CH$_2$Cl, t, J=9.2 Hz). HR-MS (ESI-TOF) calculated for $C_{16}H_{15}ClF_2N_6O_3$ 412.0862, found 413.0866 (M+H, $^{79}$Br), 415.0811 (M+H, $^{81}$Br). ESI m/z 413.1 (M+H), 344.1 (M-$C_2H_2N_3$), 289.3 (M-$C_3H_4ClO_3$), 220.1 (M-$C_5H_6ClN_3O_3$).

O-Salicylfluconazole (1l). The general synthetic method described above afforded 1l (44.0%) as an amorphous powder; mp. 142-143° C. $^1$H NMR (CDCl$_3$, 400 MHz) δ 8.31 (2H, s), 8.05 (1H, d, J=8.3 Hz), 7.93 (2H, s), 7.56-7.50 (1H, m), 7.31-7.22 (2H, m), 7.07-6.92 (2H, m), 6.87-6.78 (1H, m), 5.21 (2H, d, J=15.1 Hz), 5.08 (2H, d, J=15.1 Hz), 2.15 (3H, s). ESI m/z 469.0 (M+H), 426.9 (M-$C_2H_3O$+H), 399.9 (M-$C_2H_2N_3$), 289.3 (M-$C_9H_7O_4$), 220.1 (M-$C_{11}H_9N_3O_4$).

(iii) General procedure for the synthesis of phosphate triester derivatives of FLC (2a-h). 2-Cyanoethyl N,N-diisopropylchlorophosphoramidite (267 μL, 1.2 mmol) (for 2a-e) or m ethyl N,N-diisopropylchlorophosphoramidite (240 μL, 1.2 m mol) (for 2f-h) and diisopropyl ethylamine (209 μL, 1.2 mmol) were added to a solution of alcohol (ROH) (1.0 mmol) in dry DCM (2 mL) under a N$_2$ atmosphere. After stirring for 20 hours, the reaction mixture was partitioned between EA (10 mL) and distilled water (10 mL). The organic layer was then washed with brine (10 mL) and dried over anhydrous MgSO$_4$. The solvent was removed in vacuo and the syrup was dried under vacuum overnight. FLC (200 mg, 0.6 mmol) and 1H-tetrazole (84 mg, 1.2 mmol) were dissolved in dry dichloromethane (DCM, 2 mL) under a N$_2$ atmosphere. The syrup was dissolved in dry DCM (1 mL) and was added to this reaction mixture. After stirring for 3 hours, the reaction was cooled to 0° C. and t-butyl hydroperoxide (0.3 mL) was added. After stirring for 1 hour, the reaction mixture was partitioned between EA (10 mL) and distilled water (10 mL). The organic phase was then washed with brine (10 mL) and dried over anhydrous MgSO$_4$. The solvent was removed in vacuo. The syrup residue was purified by silica gel column chromatography, eluting with hexane and acetone from 3:1 (v/v) to 1:1 (v/v) to yield 2a-h (Scheme 3).

2-Cyanoethyl-n-undecanyl fluconazole phosphate (2a). The general synthetic method described above afforded 2a (24.0%) as a wax; mp. 75.4-77.0° C.; $^1$H NMR (CDCl$_3$, 400 MHz) δ 8.31 (2H, s), 7.93 (2H, s), 7.22-7.15 (1H, m), 6.94-6.83 (1H, m), 6.83-6.72 (1H, m), 5.21 (2H, d, J=14.2 Hz), 5.03 (2H, d, J=14.4 Hz), 4.15 (2H, —OCH$_2$CH$_2$CN, t, J=7.2 Hz), 3.93 (2H, —OCH$_2$—, t, J=7.7 Hz), 2.74 (2H, —OCH$_2$CH$_2$CN, t, J=7.2 Hz), 1.57 (2H, —OCH$_2$CH$_2$CH$_2$—, t, J=7.6 Hz), 1.41-1.27 (16H, methylene envelope), 0.92-0.83 (3H, m). HR-MS (ESI-TOF) calculated for C$_{27}$H$_{38}$F$_2$N$_7$O$_4$P 593.2691, found 594.2710 (M+H).

2-Cyanoethyl-ω-undecylenyl fluconazole phosphate (2b). The general synthetic method described above afforded 2b (36.1%) as a wax; mp. 72.6-73.6° C.; $^1$H NMR (CDCl$_3$, 400 MHz) δ 8.35 (2H, s), 7.95 (2H, s), 7.20-7.10 (1H, m), 6.91-6.81 (1H, m), 6.81-6.71 (1H, m), 5.88-5.75 (1H, CH$_2$=CH—, m), 5.23 (2H, d, J=15.1 Hz), 5.05 (2H, d, J=15.2 Hz), 5.01-4.85 (2H, CH$_2$=CH—, m), 4.20 (2H, —OCH$_2$CH$_2$CN, t, J=7.5 Hz), 3.98 (2H, —OCH$_2$—, t, J=7.8 Hz), 2.72 (2H, —OCH$_2$CH$_2$CN, t, J=7.5 Hz), 2.11-2.00 (2H, CH$_2$=CHCH$_2$—, m), 1.58 (2H, —OCH$_2$CH$_2$CH$_2$—, t, J=7.2 Hz), 1.40-1.15 (12H, methylene envelope). HR-MS (ESI-TOF) calculated for C$_{27}$H$_{36}$F$_2$N$_7$O$_4$P 591.2534, found 592.2541.

11-Bromoundecanyl-2-cyanoethyl fluconazole phosphate (2c). The general synthetic method described above afforded 2c (28.1%) as a wax; mp. 77.2-78.9° C.; $^1$H NMR (CDCl$_3$, 400 MHz) δ 8.32 (2H, s), 7.88 (2H, s), 7.20-7.10 (1H, m), 6.92-6.82 (1H, m), 6.82-6.71 (1H, m), 5.22 (2H, d, J=16.0 Hz), 5.05 (2H, d, J=16.0 Hz), 4.15 (2H, —OCH$_2$CH$_2$CN, t, J=8.1 Hz), 3.98 (2H, —OCH$_2$—, t, J=6.4 Hz), 3.43 (2H, —CH$_2$Br, t, J=8.0 Hz), 2.71 (2H, —OCH$_2$CH$_2$CN, t, J=8.1 Hz), 1.88-1.80 (2H, —CH$_2$CH$_2$Br, m,), 1.75-1.63 (2H, COCH$_2$CH$_2$—, m), 1.43-1.21 (14H, m, methylene envelope). HR-MS (ESI-TOF) calculated for C$_{27}$H$_{37}$BrF$_2$N$_7$O$_4$P 671.1796, found 672.1855 (M+H, $^{79}$Br), 674.1819 (M+H, $^{79}$Br).

2-Cyanoethyl-tetradecanyl fluconazole phosphate (2d). The general synthetic method described above afforded 2d (27.3%) as a wax; mp. 79.2-83.5° C.; $^1$H NMR (CDCl$_3$, 400 MHz) δ 8.33 (2H, s), 7.88 (2H, s), 7.20-7.11 (1H, m), 6.90-6.80 (1H, m), 6.80-6.71 (1H, m), 5.22 (2H, d, J=14.9 Hz), 5.10 (2H, d, J=14.8 Hz), 4.18 (2H, —OCH$_2$CH$_2$CN, t, J=7.8 Hz), 3.96 (2H, —OCH$_2$—, t, J=7.4 Hz), 2.78 (2H, —OCH$_2$CH$_2$CN, t, J=7.7 Hz), 1.56 (2H, —OCH$_2$CH$_2$CH$_2$—, t, J=7.4 Hz), 1.38-1.18 (22H, methylene envelope), 0.86 (3H, t, J=7.5 Hz). HR-MS (ESI-TOF) calculated for C$_{30}$H$_{44}$F$_2$N$_7$O$_4$P 635.3160, found 636.3221 (M+H). ESI m/z 636.4 (M+H).

2-Cyanoethyl-n-octyl fluconazole phosphate (2e). The general synthetic method described above afforded 2e (3.9%) as a syrup; $^1$H NMR (CDCl$_3$, 400 MHz) δ 8.35 (2H, s), 7.91 (2H, s), 7.12-7.22 (1H, m), 6.95-6.85 (1H, m), 6.85-6.75 (1H, m), 5.23 (2H, d, J=15.1 Hz), 5.07 (2H, d, J=15.1 Hz), 4.18 (2H, —OCH$_2$CH$_2$CN, t, J=6.8 Hz), 3.95 (2H, —OCH$_2$—, t, J=8.3 Hz), 2.70 (2H, —OCH$_2$CH$_2$CN, t, J=6.8 Hz), 1.61 (2H, —OCH$_2$CH$_2$CH$_2$—, t, J=8.3 Hz), 1.38-1.25 (10H, methylene envelope), 0.86 (3H, t, J=7.7 Hz). HR-MS (ESI-TOF) calculated for C$_{24}$H$_{32}$F$_2$N$_7$O$_4$P 551.2211, found 552.2219 (M+H).

Methyl-undecanyl fluconazole phosphate (2f). The general synthetic method described above afforded 2f (28.0%) as a syrup; $^1$H NMR (CDCl$_3$, 400 MHz) δ 8.33 (2H, s), 7.95 (2H, s), 7.21-7.14 (1H, m), 6.93-6.82 (1H, m), 6.82-6.73 (1H, m), 5.25 (2H, d, J=14.7 Hz), 5.05 (2H, d, J=14.7 Hz), 3.94 (2H, —OCH$_2$—, t, J=7.8 Hz), 3.41 (3H, —OCH$_3$, s), 1.59 (2H, —OCH$_2$CH$_2$CH$_2$—, t, J=7.6 Hz), 1.45-1.22 (16H, methylene envelope), 0.89 (3H, t, J=7.2 Hz). ESI m/z 555.2 (M+H).

Methyl-ω-undecylenyl fluconazole phosphate (2g). The general synthetic method described above afforded 2g (36.7%) as a syrup; $^1$H NMR (CDCl$_3$, 400 MHz) δ 8.31 (2H, s), 7.92 (2H, s), 7.21-7.11 (1H, m), 6.93-6.83 (1H, m), 6.82-6.72 (1H, m), 5.87-5.71 (1H, CH$_2$=CH—, m), 5.25 (2H, d, J=15.4 Hz), 5.05 (2H, d, J=15.5 Hz), 5.06-4.89 (2H, CH$_2$=CH—, m), 3.96 (2H, —OCH$_2$—, t, J=7.8 Hz), 3.40 (3H, —OCH$_3$, s), 2.15-2.03 (2H, CH$_2$=CHCH$_2$—, m), 1.58 (2H, —OCH$_2$CH$_2$CH$_2$—, t, J=7.2 Hz), 1.43-1.17 (12H, methylene envelope). ESI m/z 553.4 (M+H).

Methyl-n-octyl fluconazole phosphate (2h). The general synthetic method described above afforded 2h (38%) as a syrup; $^1$H NMR (CDCl$_3$, 400 MHz) δ 8.23 (2H, s), 7.99 (2H, s), 7.25-7.16 (1H, m), 7.01-6.91 (1H, m), 6.87-6.71 (1H, m), 5.25 (2H, d, J=14.7 Hz), 5.11 (2H, d, J=14.7 Hz), 3.99 (2H, —OCH$_2$—, t, J=7.8 Hz), 3.57 (3H, OCH$_3$, s), 1.69 (2H, —OCH$_2$CH$_2$CH$_2$—, t, J=8.1 Hz), 1.43-1.29 (10H, methylene envelope), 0.91 (3H, t, J=8.3 Hz). MS (ESI) calculated for C$_{22}$H$_{31}$F$_2$N$_6$O$_4$P 512.2, found 513.2 (M+H).

(iv) General procedure for the synthesis of phosphate diester derivatives of FLC (3a-d). Ammonium hydroxide (57 μL, 0.48 mmol) was added to a solution of compound 2 (114.8 mg, 0.19 mmol) in methanol (1 mL) and DCM (1 mL). After stirring for 24 hours, the solvent was evaporated in vacuo. The syrup residue was centrifuged and lyophilized to afford 3 (Scheme 2).

n-Undecanyl fluconazole phosphate (3a). The general synthetic method described above afforded 3a (65.6%) as a syrup; $^1$H NMR (CDCl$_3$, 400 MHz) δ 8.28 (2H, s), 7.91 (2H, s), 7.21-7.13 (1H, m), 6.92-6.82 (1H, m), 6.82-6.71 (1H, m), 5.20 (2H, d, J=15.3 Hz), 5.01 (2H, d, J=15.4 Hz), 3.95 (2H, —OCH$_2$—, t, J=8.1 Hz), 1.59 (2H, —OCH$_2$CH$_2$CH$_2$—, t, J=8.1 Hz), 1.41-1.27 (16H, methylene envelope), 0.95-0.86 (3H, m). HR-MS (ESI-TOF) calculated for C$_{24}$H$_{35}$F$_2$N$_6$O$_4$P 540.2425, found 541.2431 (M+H).

ω-Undecylenyl fluconazole phosphate (3b). The general synthetic method described above afforded 3b (65.2%) as a syrup; $^1$H NMR (CDCl$_3$, 400 MHz) δ 8.28 (2H, s), 7.88 (2H, s), 7.15-7.00 (2H, m), 6.89-6.75 (1H, m), 5.89-5.76 (1H, CH$_2$=CH—, m), 5.25 (2H, d, J=14.2 Hz), 5.03 (2H, d, J=14.2 Hz), 5.00-4.86 (2H, CH$_2$=CH—, m), 3.99 (2H, —OCH$_2$—, t, J=8.1 Hz), 2.10-1.99 (2H, CH$_2$=CHCH$_2$—, m), 1.60 (2H, —OCH$_2$CH$_2$CH$_2$—, t, J=7.5 Hz), 1.44-1.18 (12H, methylene envelope). HR-MS (ESI-TOF) calculated for C$_{24}$H$_{33}$F$_2$N$_6$O$_4$P 538.2269, found 539.2270 (M+H).

11-Bromoundecanyl fluconazole phosphate (3c). The general synthetic method described above afforded 3c (100.0%) as a syrup; $^1$H NMR (CDCl$_3$, 400 MHz) δ 8.26 (2H, s), 7.89 (2H, s), 7.12-7.00 (1H, m), 6.93-6.84 (1H, m), 6.83-6.72 (1H, m), 5.20 (2H, d, J=14.9 Hz), 5.02 (2H, d, J=14.9 Hz), 3.91 (2H, —OCH$_2$—, t, J=8.4 Hz), 3.47 (2H, —CH$_2$Br, t, J=7.8 Hz), 1.87-1.81 (2H, —CH$_2$CH$_2$Br, m), 1.76-1.65 (2H, COCH$_2$CH$_2$—, m), 1.45-1.23 (14H, m, methylene envelope). ESI m/z 619.2 (M+H, $^{79}$Br), 621.2 (M+H, $^{81}$Br).

n-Tetradecanyl fluconazole phosphate (3d). The general synthetic method described above afforded 3d (100.0%) as a syrup; $^1$H NMR (CDCl$_3$, 400 MHz) δ 8.25 (2H, s), 7.86 (2H, s), 7.18-7.09 (1H, m), 6.92-6.83 (1H, m), 6.82-6.73 (1H, m), 5.20 (2H, d, J=15.1 Hz), 4.99 (2H, d, J=14.9 Hz), 3.97 (2H, —OCH$_2$—, t, J=7.7 Hz), 1.57 (2H, —OCH$_2$CH$_2$CH$_2$—, t, J=7.7 Hz), 1.41-1.98 (22 H, methylene envelope), 0.88 (3H, t, J=7.9 Hz). ESI m/z 583.3 (M+H)$^+$.

(v) General procedure for the synthesis of carbohydrate phosphate triester derivatives of FLC (4a and 4b). Benzylamine (BnNH$_2$) (163 μL, 1.5 mmol) was added to a solution of β-D-glucosepentaacetate (7a) or 2-acetamido-2-deoxy-1,3,4,6-tetra-O-acetyl-β-D-glucopyranoside (7b) (1 mmol) in THF (3 mL). After stirring overnight, the reaction mixture was diluted with cold, distilled water and extracted with DCM twice (2×5 mL). The combined organic phase was respectively washed with ice-cold diluted hydrochloric acid, saturated sodium bicarbonate (5 mL), brine (5 mL), and distilled water (5 mL). The combined extracts were dried (MgSO$_4$) and the solvent was removed in vacuo. The syrup was dried in a vacuum overnight to afford 8a and 8b (Scheme 3). 2-Cyanoethyl N,N-diisopropylchlorophosphoramidite (236.7 μL, 1 mmol) and diisopropyl ethylamine (174.3 μL, 1 mmol) were added to a solution of 8a or 8b (0.5 mmol) in dry DCM (2 mL). After stirring for 20 hours, the reaction mixture was extracted with EA (10 mL) and distilled water (10 mL). The organic phase was then washed with brine (10 mL) and dried (MgSO$_4$). The solvent was removed in vacuo and the syrup was dried under vacuum overnight to yield 9a and 9b (Scheme 3). FLC (100 mg, 0.3 mmol) and 1H-tetrazole (42 mg, 0.6 mmol) were dissolved in dry DCM (1 mL) under a N$_2$ atmosphere. The syrup (9a or 9b) was dissolved in dry DCM (0.5 mL) and added to the reaction mixture. After stirring for 3 hours, the reaction mixture was cooled to 0° C. and t-butyl hydroperoxide (0.15 mL) was added. After stirring for 1 hour, the reaction mixture was partitioned between EA (10 mL) and distilled water (10 mL). The organic layer was then washed with brine (10 mL) and dried (MgSO$_4$). The solvent was removed in vacuo. The syrup residue was purified using silica gel column chromatography, eluting with hexane-acetone from 2:1 (v/v) to 1:1 (v/v) to afford 4a or 4b (Scheme 3).

2-Cyanoethyl-[1-(β-D-2,3,4,6-glucosyltetraacetate)]fluconazole phosphate (4a). The general synthetic method described above afforded 4a (13.9%) as a syrup; $^1$H NMR (CDCl$_3$, 400 MHz) δ 7.73 (2H, s), 7.56 (2H, s), 7.55-7.21 (3H, m), 5.95-5.82 (1H, anomeric proton, m), 5.60-5.42 (2H, m), 5.10 (2H, d, J=15.1 Hz), 4.90 (2H, d, J=15.1 Hz), 4.41-4.08 (6H, m), 2.78 (2H, —OCH$_2$CH$_2$CN, t, J=7.8 Hz), 2.15-2.10 (12H, overlap). HR-MS (ESI-TOF) calculated for C$_{30}$H$_{34}$F$_2$N$_7$O$_{13}$P 769.1920, found 770.1927 (M+H).

2-Cyanoethyl-[1-(2-acetamido-2-deoxy-3,4,6-tri-O-acetyl-β-D-glucopyranosidyl)]fluconazole phosphate (4b). The general synthetic method described above afforded 3b (8.3%) as a wax; $^1$H NMR (CDCl$_3$, 400 MHz) δ 7.81 (2H, s), 7.59 (2H, s), 7.52-7.19 (3H, m), 5.91-5.80 (1H, anomeric proton, m), 5.59-5.43 (2H, m), 5.05 (2H, d, J=14.7 Hz), 4.92 (2H, d, J=14.7 Hz), 4.42-4.33 (2H, m), 4.39-4.05 (4H, m), 2.75 (2H, —OCH$_2$CH$_2$CN, t, J=7.3 Hz), 2.12-2.06 (12H, overlap). HR-MS (ESI-TOF) calculated for C$_{30}$H$_{35}$F$_2$N$_8$O$_{12}$P 768.2080, found 769.2068 (M+H).

Synthesis and Antifungal Activities of Fluconazole Derivatives

Scheme 4.
Synthetic methods for conversion of the hydroxyl group in Fluconazole (10) to other functional groups.

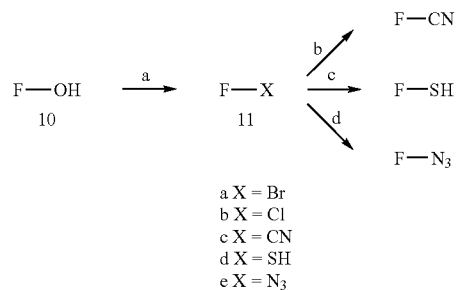

a X = Br
b X = Cl
c X = CN
d X = SH
e X = N$_3$

Reagents and conditions: (SOBr$_2$ or SOCl$_2$, ACCN, immidazole; (b) toluene, SnCl$_2$, TMSCN, rt, 3 h; (c) Na$_2$S, DMF; (d) SnCl$_2$, TMSN$_3$, rt, 3 h.

Experimental

1) Synthesis of FBr (11a)

A solution of 1.94 g of imidazole in 15 ml of dry acetonitrile at 0° C. was treated with 1 ml of thionyl bromide and then with 1.63 g of 1,3-bis(1H-1,2,4-triazol-1-yl)-2-(2,4-difluorophenyl)-propan-2-ol (fluconazole). The resulting mixture was stirred for 2-3 hours. The residue obtained after evaporation of the solvent in vacuo was partitioned between methylene chloride (~100 mL) and cold 5% aqueous sodium bicarbonate (~100 mL), and the organic extract (~100 ml) was successively washed with aqueous sodium bicarbonate (50 mL), brine (50 mL) and dried (by anhydrous sodium sulfate). Removal of methylene chloride followed by flash chromatography of the residue on silica (100 g) and elution with 97% ethyl acetate/3% diethylamine yielded the title compound, which was crystallised from ethyl acetate/hexane. Amorphous powder; Yield: 48%; ESI m/z 367.2 ((M+H)$^+$, $^{79}$Br), 370.2 ((M+H)$^+$, $^{81}$Br). $^1$H NMR (CDCl$_3$, 400 MHz) δ 8.02 (2H, s), 7.91 (2H, s), 6.94-6.78 (3H, m), 5.25 (2H, d, J=12.5 Hz), 5.11 (2H, d, J=12.5 Hz).

1) Synthesis of FCl (11b)

A solution of 1.94 g of imidazole in 15 ml of dry acetonitrile at 0° C. was treated with 1 ml of thionyl chloride and then with 1.63 g of 1,3-bis(1H-1,2,4-triazol-1-yl)-2-(2,4-difluorophenyl)-propan-2-ol (fluconazole). The resulting mixture was stirred for 2-3 hours. The residue obtained after evaporation of the solvent in vacuo was partitioned between methylene chloride (~100 mL) and cold 5% aqueous sodium bicarbonate (~100 mL), and the organic extract (~100 ml) was successively washed with aqueous sodium bicarbonate (50 mL), brine (50 mL) and dried (by anhydrous sodium sulfate). Removal of methylene chloride followed by flash chromatography of the residue on silica (100 g) and elution with 97% ethyl acetate/3% diethylamine yielded the title compound, which was crystallised from ethyl acetate/hexane. Amorphous powder; Yield: 65%; ESI m/z 325.1 (M+H)+. $^1$H NMR (CDCl$_3$, 400 MHz) δ 8.04 (2H, s), 7.92 (2H, s), 6.95-6.81 (3H, m), 5.17 (2H, d, J=13.2 Hz), 5.09 (2H, d, J=13.2 Hz).

3. Synthesis of FCN (11c)

To a solution of FBr (369 mg, 1 mmol) in dry toluene (5 mL) at 0° C. was added dropwise SnCl$_2$ (50 μL) followed by trimethylsilyl cyanide (3 M solution in toluene, 1 mL, 3 mmol). The mixture was stirred at room temperature for 3 h, then MeOH (1 mL) was added. The mixture was suspended in water (10 mL) and extracted with DCM (10 mL). The organic layer was washed with sodium bicarbonate (5%, 10 mL) and brine (10 mL), then dried under anhydrous sodium sulfate. The expected product was purified over a silica gel colum eluting with hexane/acetone (2/1). Amorphous powder; Yield: 35%; ESI m/z 316.3 (M+H)+. $^1$H NMR (CDCl$_3$, 400 MHz) δ 8.03 (2H, s), 7.95 (2H, s), 6.95-6.84 (1H, m), 6.77-6.66 (2 H, m) 5.07 (2H, d, J=12.5 Hz), 4.99 (2H, d, J=12.5 Hz).

4. Synthesis of FSH (11d)

To a solution of FBr (369 mg, 1 mmol) in dry DMF (5 mL) at 0° C. was added sodium sulfide (110 mg, 2 mmol). The mixture was stirred at room temperature for 24 h. The mixture was suspended in water (10 mL) and extracted with ethyl acetate (10 mL). The organic layer was washed with brine (10 mL), then dried under anhydrous sodium sulfate. The expected product was purified over a silica gel colum eluting with hexane/acetone (1/1). Amorphous powder; Yield: 88%; ESI m/z 322.3 (M+H)+. $^1$H NMR (CDCl$_3$, 400 MHz) δ 7.99 (2H, s), 7.91 (2H, s), 6.90-6.88 (1H, m), 6.79-6.71 (2 H, m) 6.23 (1H, s), 5.05 (2H, d, J=14.5 Hz), 4.95 (2H, d, J=14.5 Hz).

5. Synthesis of FN$_3$ (11e)

To a solution of FBr (369 mg, 1 mmol) in dry toluene (5 mL) at 0° C. was added dropwise SnCl$_2$ (50 μL) followed by trimethylsilyl azide (3 M solution in toluene, 1 mL, 3 mmol). The mixture was stirred at room temperature for 3 h, then MeOH (1 mL) was added. The mixture was suspended in water (10 mL) and extracted with DCM (10 mL). The organic layer was washed with sodium bicarbonate (5%, 10 mL) and brine (10 mL), then dried under anhydrous sodium sulfate. The expected product was purified over a silica gel colum eluting with hexane/acetone (2/1). Amorphous powder; Yield: 31%; ESI m/z 332.3 (M+H)+. $^1$H NMR (CDCl$_3$, 400 MHz) δ 8.07 (2H, s), 7.94 (2H, s), 6.91-6.88 (1H, m), 6.79-6.71 (1 H, m), 6.66-6.55 (1H, m), 5.11 (2H, d, J=11.5 Hz), 5.03 (2H, d, J=11.5 Hz).

TABLE 5

General structure, physicochemical properties and antifungal activity (MIC values, μg/mL)[a] against *Candida albicans* (RPMI and SDB), *Cryptococcus neoformans* (SDB), and *Aspergillus niger* (SDB) at 35-37° C. after 24-48 h and for carboxylic acid ester derivatives of FLC (1).

| X | C. albicans ATCC 14053, RPMI | C. albicans, ATCC 14053, SDB | C. neoformans ATCC 66031, SDB | A. niger ATCC 16404, SDB | Log P[b] | Kp (μ/hr)[c] |
|---|---|---|---|---|---|---|
| SH | ND | 1,862 | 339 | >3,728 | 1.66 | 3.12 |
| Cl | 1,137 | >883 | 28 | 883 | 1.97 | 5.01 |
| Br | 701 | >701 | 22 | 701 | 2.06 | 3.11 |
| I | 749 | >749 | 47 | 749 | 2.48 | 3.16 |
| Mesyl | 645 | 1,290 | 40 | 1,290 | 0.23 | 0.13 |
| Tosyl | 365 | >731 | 46 | >731 | 2.35 | 1.38 |
| N$_3$ | >610 | >610 | 19 | 610 | -4.68 | 8.47e-05 |
| P(O)(OCH$_3$)N(CH$_3$)$_2$ | 1,294 | >1,660 | 10 | 415 | 0.97 | 2.87e-05 |
| P(O)(OBn)OH | 787 | 273 | ≦17 | 1,635 | 2.49 | 1.74e-04 |
| P(O)(OBn)$_2$ | ND | >1,020 | 127 | NT | 3.57 | 2.87e-04 |
| P(O)(OtBu)$_2$ | ND | 787 | 196 | 787 | 2.88 | 2.41e-04 |
| FLC | 2.3 | ≧4,444 | 2.4 | >580 | 0.25 | 0.39 |
| AMB | 0.7 | 1.5 | <3.7 | 0.4 | -3.76 | 5.08 × 10$^{-8}$ |
| DMSO | >5,000 | >5,000 | >5,000 | >5,000 | | |

[a]The result is the average of three separate experiments;
[b]Partition coefficient of the compound calculated using the KowWin program;
[c]Dermal permeability coefficient of the compound calculated using the DermWin program (μ/hour).

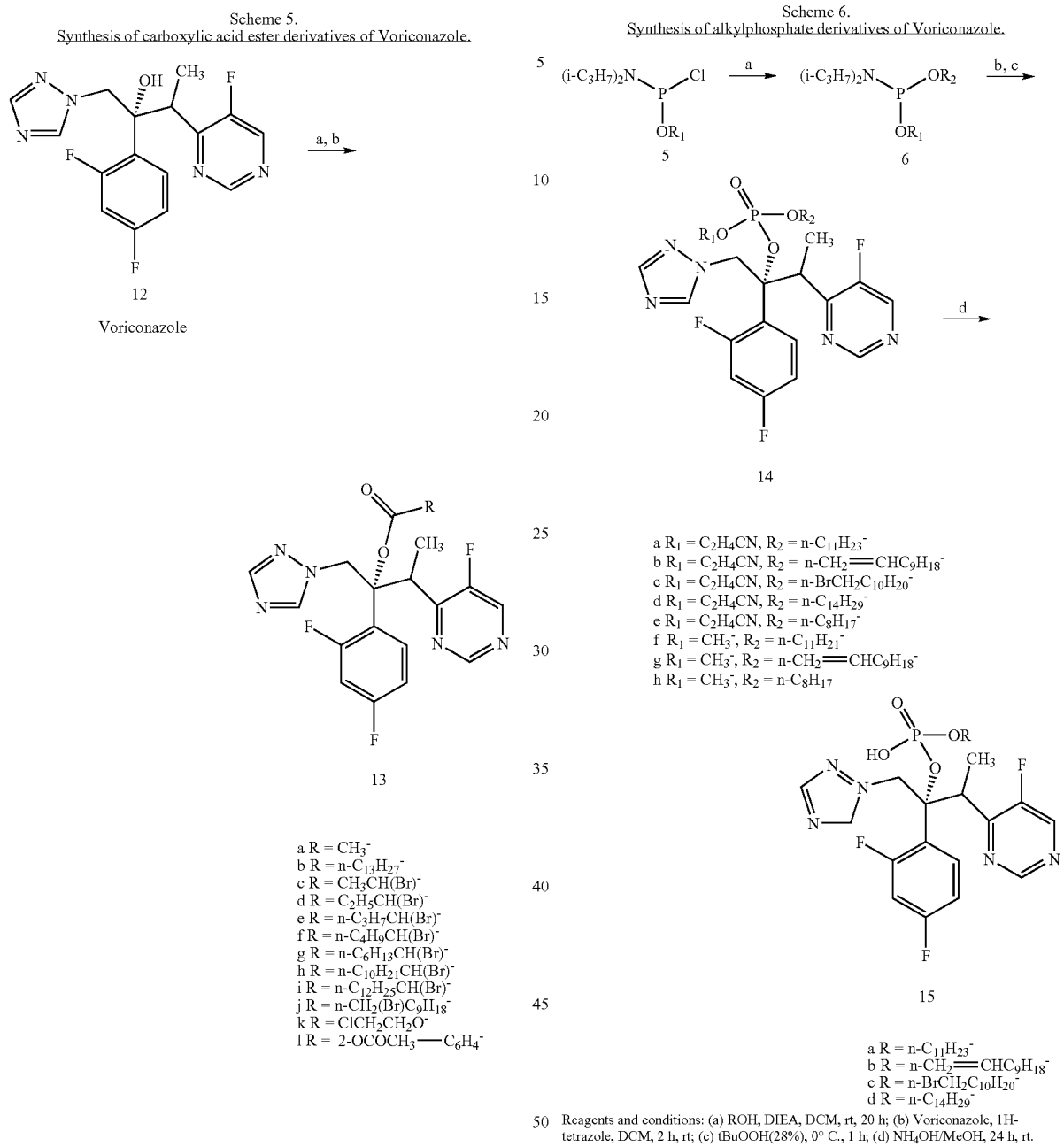

Scheme 5.
Synthesis of carboxylic acid ester derivatives of Voriconazole.

12 Voriconazole

13 a R = CH₃⁻
b R = n-C₁₃H₂₇⁻
c R = CH₃CH(Br)⁻
d R = C₂H₅CH(Br)⁻
e R = n-C₃H₇CH(Br)⁻
f R = n-C₄H₉CH(Br)⁻
g R = n-C₆H₁₃CH(Br)⁻
h R = n-C₁₀H₂₁CH(Br)⁻
i R = n-C₁₂H₂₅CH(Br)⁻
j R = n-CH₂(Br)C₉H₁₈⁻
k R = ClCH₂CH₂O⁻
l R = 2-OCOCH₃—C₆H₄⁻

Reagents and conditions: (a) NaH, DMF, rt, 2 h; (b) RCOCl, rt, 3 h.

Scheme 5 shows a procedure for the preparation of carboxylic acid ester derivatives of Voriconazole (13a-l) from the reaction of acyl chlorides with Voriconazole in the presence of sodium hydride. Acyl chlorides can be synthesized from the corresponding carboxylic acids with thionyl chloride in dry benzene if they are not commercially available.

Scheme 6.
Synthesis of alkylphosphate derivatives of Voriconazole.

14 a R₁ = C₂H₄CN, R₂ = n-C₁₁H₂₃⁻
b R₁ = C₂H₄CN, R₂ = n-CH₂=CHC₉H₁₈⁻
c R₁ = C₂H₄CN, R₂ = n-BrCH₂C₁₀H₂₀⁻
d R₁ = C₂H₄CN, R₂ = n-C₁₄H₂₉⁻
e R₁ = C₂H₄CN, R₂ = n-C₈H₁₇⁻
f R₁ = CH₃⁻, R₂ = n-C₁₁H₂₁⁻
g R₁ = CH₃⁻, R₂ = n-CH₂=CHC₉H₁₈⁻
h R₁ = CH₃⁻, R₂ = n-C₈H₁₇

15 a R = n-C₁₁H₂₃⁻
b R = n-CH₂=CHC₉H₁₈⁻
c R = n-BrCH₂C₁₀H₂₀⁻
d R = n-C₁₄H₂₉⁻

Reagents and conditions: (a) ROH, DIEA, DCM, rt, 20 h; (b) Voriconazole, 1H-tetrazole, DCM, 2 h, rt; (c) tBuOOH(28%), 0° C., 1 h; (d) NH₄OH/MeOH, 24 h, rt.

Scheme 6 demonstrates a preparation of phosphate triester derivatives of Voriconazole (14a-h). The reaction of alcohol (ROH) with phosphorylating reagents, cyanoethyl N,N-diisopropylchlorophosphoramidite or methyl N,N-diisopropylchlorophosphoramidite (5), in the presence of diisopropyl ethylamine in dry DCM will give N,N-disopropylamine phosphine derivatives (6). Coupling reactions of Voriconazole with 6 in the presence of 1-H-tetrazole in DCM followed by oxidation with t-butyl hydroperoxide will afford phosphate triesters (14a-h). The cyanoethyl protecting group in 14a-d can be cleaved using ammonium hydroxide to yield the corresponding phosphate diester derivatives of Voriconazole (15a-d).

Scheme 7.
Synthesis of carbohydrate phosphate triester derivatives of Voriconazole.

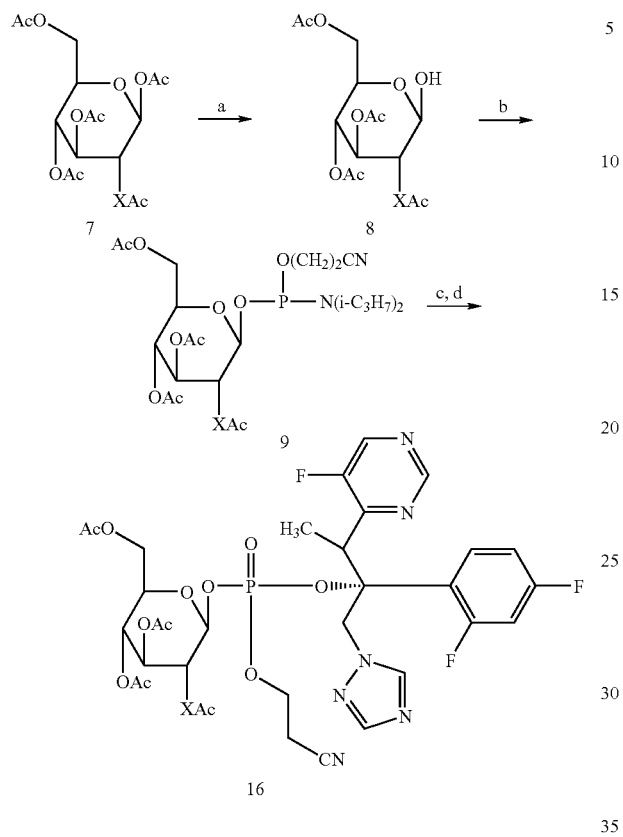

16
a X = O
b X = NH

Reagents and conditions: (a) BnHN₂, THF; (b) 2-cyanoethyl N,N-diisopropylchlorophosphoramidite, DIEA, DCM, 20 h; (c) 1. Voriconazole, 1H-tetrazole, DCM, 2 h, rt; (d) tBuOOH, 0° C., 1 h.

Scheme 7 displays a synthesis of carbohydrate phosphate triester derivatives of Voriconazole (16a and 16b). The reaction of β-D-glucosepentaacetate (7a) or 2-acetamido-2-deoxy-1,3,4,6-tetra-O-acetyl-β-D-glucopyranoside (7b) with benzylamine in THF will result in the selective removal of the anomeric O-acetyl group to produce the reducing carbohydrates 8a and 8b. Reaction of 8 with cyanoethyl N,N-diisopropylchlorophosphoramidite followed by coupling with Voriconazole and oxidation reaction in the presence of t-butyl hydroperoxide will furnish carbohydrate phosphate triesters (16a and 16b).

Scheme 8.
Synthetic methods for conversion of the hydroxyl group in Voriconazole (12) to other functional groups.

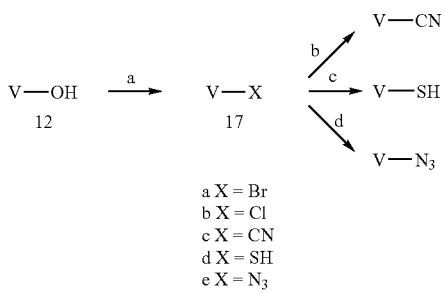

a X = Br
b X = Cl
c X = CN
d X = SH
e X = N₃

Reagents and conditions: (SOBr₂ or SOCl₂, ACCN, immidazole; (b) toluene, SnCl₂, TMSCN, rt, 3 h; (c) Na₂S, DMF; (d) SnCL₂, TMSN₃, rt, 3 h.

Scheme 9.
Synthesis of phosphite and phosphate derivatives of Fluoconazole.

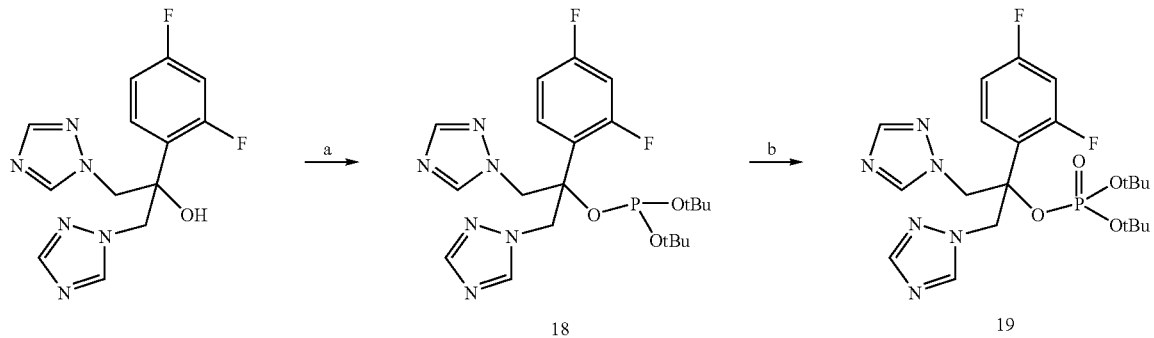

-continued

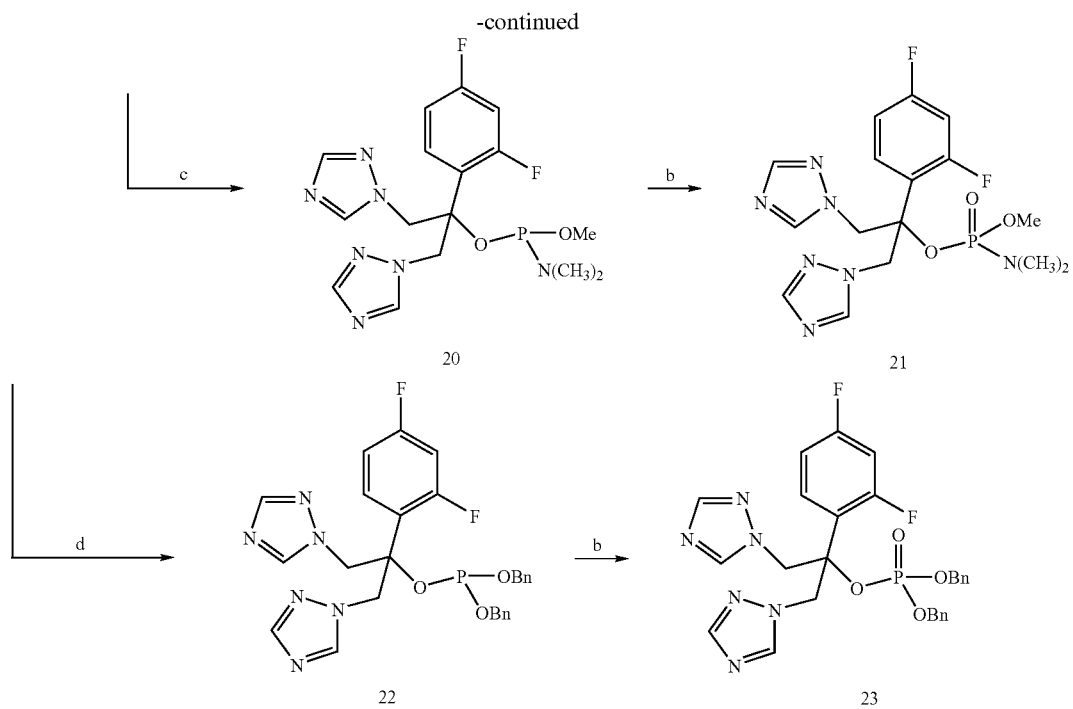

Reagents and conditions: (a) P(OtBu)$_2$N(iPr)$_2$, 1-H-tetrazole, THF;
(b) t-BuOOH, TFH; (c) PCl(OMe)N(CH$_3$)$_2$, DIPEA, THF;
(d) PCl(OBn)$_2$, DIPEA, THF.

Reagents and conditions for the Voriconazole and fluconazole derivatives provided in schemes 8 and 9 are set forth therein respectively.

Physicochemical Properties

Physicochemical properties were estimated using the KowWin program (Version 1.67) and estimation methodology developed at Syracuse Research Corporation (Environmental Chemistry Center, KOWWIN—The Octanol-Water Partition Coefficient Program, PC-Computer software, Running Ridge Road, North Syracuse, N.Y., 1999). The LogKow (KowWin) program estimates the log octanol/water partition coefficient (log P) of organic chemicals using an atom/fragment contribution method. Meylan, W. M., et al., *J. Pharm. Sci.* 1995, 84, 83. KowWin uses a "fragment constant" methodology to predict log P. In a "fragment constant" method, a structure is divided into fragments (atom or larger functional groups) and coefficient values of each fragment or group are summed together to yield the log P estimate. To confirm the validity of the log P calculation, the reported experimental data were compared with acquired data for some of the compounds. The experimental data were in agreement with the calculated log P values.

The Dermal Permeability Coefficient Program (DermWin Version 1.43) was used to estimate the dermal permeability coefficient (Kp) and the dermally absorbed dose per event (DAevent) of organic compounds. DermWin estimates a LogKow for every SMILES notation by using the estimation engine from the KowWin Program based on the general equation, LogKp=−2.72+0.71 LogKow−0.0061 MW, where LogKow and MW are estimated partition coefficient and molecular weight for each compound.

The HYDROWIN (Version 1.67) (Mill, T., et al., EPZ Contract No. 68-02-4254. Menlo Park, Calif.: SRI International 1987) was used to estimate the half-lives based on the total acid-catalyzed rate constant and the prediction methodology developed for the U.S. Environment Protection Agency. The half-lives for acid-catalyzed rate constants were calculated at pH 5.6 from the general equation, Half-life=0.6931/(Kb)(1.0E-8.4), where 1.0E-8.4 is the OH$^-$ concentration in water at pH 5.6.

In vitro Antifungal Activity

Microorganisnis. *C. albicans* ATCC 14053, *A. niger* ATCC 16404, and *C. neoformans* ATCC 66031 were obtained from American Type Culture Collection, Manassas, Va. Stock cultures were kept on Sabouraud dextrose agar (SDA; Becton-Dickinson and Co., Sparks, Md.). Subcultures were prepared on SDA at 35-37° C. Suspension cultures were prepared by inoculation of single colonies in 7 ml of normal saline solution. Prior to preparation of susceptibility assays, yeast cells were resuspended in normal saline to make a transmittance of 73-75% at 530 nm that provide equivalent concentration of 10$^6$ cells/ml and spores of *A. niger* in saline medium to produce a similar transmittance at 530 nm compared to the control tube. The media were RPMI (RPMI 1640; ICN Biomedical, Aurora, Ohio) adjusted to pH 6.9 and Sabouraud dextrose broth (SDB; Becton Dickinson and Co., Sparks, Md.).

Chemicals and Antifungal Agents

AMB was purchased from Acros, New Jersey, USA, and was kept as a 5 μM stock in DMSO at 0° C. and used during one week of preparation. FLC was purchased from Medisa Inc., New York, USA, or was provided from Vera Laboratories Ltd, Hyderabad, India, and was kept as a 20 μM stock solution at 0° C. Test compounds were dissolved in DMSO (0.56 mg/ml) and stored at 0° C. Working dilutions were made in RPMI or SDB medium. Higher concentrations of compound were used for compounds with weak antifungal activities. The final maximum concentration of DMSO in the assays was 5% (v/v). DMSO was not inhibitory to the organisms in the concentrations tested.

Susceptibility Testing

Microdilutions for control experiments with *C. albicans*, *A. niger*, and *C. neoformans* were the modified method of National Committee for Clinical Laboratory Standards (NC-CLS) method as described by Galgiani and by the more recent NCCLS M27-A microdilution methods as described previously. Galgiani, J. *N. Antimicrob. Agents Chemother.* 1993, 37, 2517; National Committee for Clinical Laboratory Standards. Reference method for broth dilution antifungal susceptibility testing for yeasts. Approval standard. Document M27-A. National Committee for Clinical Laboratory Standards, Wayne, Pa., 1997, Vol. 17: no. 9; C. arballeira, N. M., et al. *Arch. Pharm.-Pharm. Med. Chem.* 2004, 337, 152. Dilutions were prepared in 0.1 ml of RPMI or SDB; the inocula were either $10^4$ *C. albicans* or *C. neoformans* cells or *A. niger* spores. The tubes were incubated for 24-48 h at 36±1° C., and turbidity was read visually. MICs were calculated in comparison to growth control as the lowest concentration that shows inhibition for AMB, FLC, and the test compounds.

All journal articles and reference citations provided above, in parentheses or otherwise, whether previously stated or not, are incorporated herein by reference.

Although the present invention has been shown and described with a preferred embodiment thereof, various changes, omissions and additions to the form and detail thereof, may be made therein, without departing from the spirit and scope of the invention.

What is claimed is:

1. A compound of the formula:

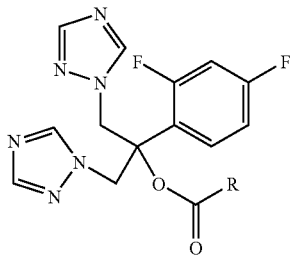

(1)

wherein R is an alkyl, aryl, alkene, alkyne, a substituted alkene, a substituted alkyl, a substituted alkyne, a substituted aryl, an alkyl halide, alkoxy or an aryloxy;

or a salt thereof.

2. A method of synthesizing the compound of the formula:

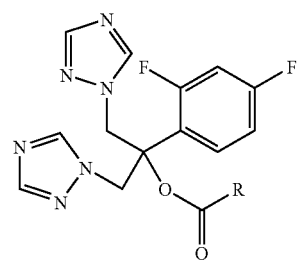

(1)

wherein R is an alkyl, aryl, alkene, alkyne, a substituted alkene, a substituted alkyl, a substituted alkyne, a substituted aryl or an alkyl halide, alkoxy or aryloxy;

adding a compound of the following formula which comprises:

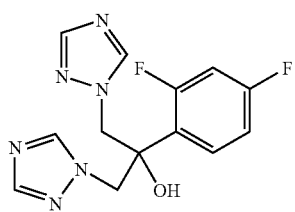

(10)

to a mixture comprised of a solvent to form a reaction mixture; and adding a carbonyl compound of the formula RCOCl wherein R is an alkyl, aryl, alkene, alkyne, a substituted alkene, a substituted alkyl, a substituted alkyne, a substituted aryl or an alkyl halide, alkoxy or aryloxy to the reaction mixture to produce (1).

* * * * *

UNITED STATES PATENT AND TRADEMARK OFFICE
CERTIFICATE OF CORRECTION

| | | |
|---|---|---|
| PATENT NO. | : 7,351,731 B2 | Page 1 of 1 |
| APPLICATION NO. | : 11/289348 | |
| DATED | : April 1, 2008 | |
| INVENTOR(S) | : Parang et al. | |

It is certified that error appears in the above-identified patent and that said Letters Patent is hereby corrected as shown below:

On the title page insert the following:

Related U.S. Application Data

(63) Continuation of application No. PCT/US2004/23316, filed on July 19, 2004.

(60) Provisional application No. 60/543,972, filed February 12, 2004 and provisional patent No. 60/488,319, filed July 18, 2003.

In column 1, at lines 6-11 the Priority Data should read as follows:

This application is a continuation of International Patent Application Serial No. PCT/US2004/23316, filed July 19, 2004 which claims priority to United States Provisional Patent Application Serial No. 60/543,972, filed February 12, 2004 and United States Provisional Patent Application Serial No. 60/488,319, filed July 18, 2003.

Signed and Sealed this

Fourth Day of November, 2008

JON W. DUDAS
*Director of the United States Patent and Trademark Office*